US008751194B2

(12) United States Patent
Panther et al.

(10) Patent No.: US 8,751,194 B2
(45) Date of Patent: Jun. 10, 2014

(54) POWER CONSUMPTION MANAGEMENT OF DISPLAY IN PORTABLE DEVICE BASED ON PREDICTION OF USER INPUT

(71) Applicant: Fitbit, Inc., San Francisco, CA (US)

(72) Inventors: Heiko Gernot Albert Panther, Oakland, CA (US); Andrew Cole Axley, Oakland, CA (US); Shelten Gee Jao Yuen, Berkeley, CA (US); Sara Yael Glick, San Francisco, CA (US); Shimona Avelina Carvalho, Oakland, CA (US); James Park, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/154,136

(22) Filed: Jan. 13, 2014

(65) Prior Publication Data

US 2014/0125619 A1 May 8, 2014

Related U.S. Application Data

(60) Continuation-in-part of application No. 13/959,714, filed on Aug. 5, 2013, which is a continuation-in-part of application No. 13/696,334, filed on Dec. 4, 2012, (Continued)

(51) Int. Cl.
*G06F 19/00* (2011.01)
*G06F 3/0488* (2013.01)
(52) U.S. Cl.
CPC .................................. *G06F 3/04883* (2013.01)
USPC ........................................................ 702/160
(58) Field of Classification Search
CPC . G06F 3/04883; G06F 1/1616; G06F 1/1641; G06F 3/0481; G06F 3/0483
USPC .................. 702/160, 150, 155, 182–185, 188
See application file for complete search history.

(56) References Cited

U.S. PATENT DOCUMENTS

| 2,717,736 A | 9/1955 | Schlesinger |
| 2,883,255 A | 4/1959 | Anderson |

(Continued)

FOREIGN PATENT DOCUMENTS

| JP | 11347021 | 12/1999 |
| WO | WO 2008/038141 | 4/2008 |
| WO | WO 2009/042965 | 4/2009 |

OTHER PUBLICATIONS

"Automatic classification of ambulatory movements and evaluation of energy consumptions utilizing accelerometers and barometer", Ohtaki, et al, Microsystem Technologies, vol. 11, No. 8-10, Aug. 2005, pp. 1034-1040.

(Continued)

*Primary Examiner* — Edward Raymond
(74) *Attorney, Agent, or Firm* — Martine Penilla Group, LLP

(57) ABSTRACT

Methods, devices, and computer programs are presented for managing power consumption of a display. One method includes an operation for setting a first display setting for a touchscreen of an activity monitoring device associated with a user. The first display setting has having a first rate of power consumption by the display and a first touchscreen scan rate for detecting touch on the touchscreen. Further, the method includes operations for receiving data at the activity monitoring device, the data being indicative of an external event, and for applying a second display setting for the touchscreen based on a predefined expected user interaction. The second display setting has a second rate of power consumption and a second touchscreen scan rate.

30 Claims, 21 Drawing Sheets

Related U.S. Application Data now Pat. No. 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, application No. 14/154,136, which is a continuation-in-part of application No. 13/959,714, filed on Aug. 5, 2013, which is a continuation-in-part of application No. 13/759,485, filed on Feb. 5, 2013, now Pat. No. 8,543,351, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, application No. 14/154,136, which is a continuation-in-part of application No. 13/959,714, filed on Aug. 5, 2013.

(60) Provisional application No. 61/388,595, filed on Sep. 30, 2010, provisional application No. 61/390,811, filed on Oct. 7, 2010, provisional application No. 61/680,230, filed on Aug. 6, 2012.

(56) References Cited

U.S. PATENT DOCUMENTS

| | | |
|---|---|---|
| 3,163,856 A | 12/1964 | Kirby |
| 3,250,270 A | 5/1966 | Bloom |
| 3,918,658 A | 11/1975 | Beller |
| 4,192,000 A | 3/1980 | Lipsey |
| 4,244,020 A | 1/1981 | Ratcliff |
| 2,284,849 A | 8/1981 | Anderson et al. |
| 4,281,663 A | 8/1981 | Pringle |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,575,804 A | 3/1986 | Ratcliff |
| 4,578,769 A | 3/1986 | Frederick |
| 4,617,525 A | 10/1986 | Lloyd |
| 4,977,509 A | 12/1990 | Pitchford et al. |
| 5,058,427 A | 10/1991 | Brandt |
| 5,224,059 A | 6/1993 | Nita et al. |
| 5,295,085 A | 3/1994 | Hoffacker |
| 5,323,650 A | 6/1994 | Fullen et al. |
| 5,446,705 A | 8/1995 | Haas et al. |
| 5,456,648 A | 10/1995 | Edinburg et al. |
| 5,583,776 A | 12/1996 | Levi et al. |
| 5,671,162 A | 9/1997 | Werbin |
| 5,704,350 A | 1/1998 | Williams, III |
| 5,724,265 A | 3/1998 | Hutchings |
| 5,890,128 A | 3/1999 | Diaz et al. |
| 5,891,042 A | 4/1999 | Sham et al. |
| 5,899,963 A | 5/1999 | Hutchings |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amano et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,529,827 B1 | 3/2003 | Beason et al. |
| 6,561,951 B2 | 5/2003 | Cannon et al. |
| 6,571,200 B1 | 5/2003 | Mault |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 7,062,225 B2 | 6/2006 | White |
| 7,162,368 B2 | 1/2007 | Levi et al. |
| 7,171,331 B2 | 1/2007 | Vock et al. |
| 7,200,517 B2 | 4/2007 | Darley et al. |
| 7,261,690 B2 | 8/2007 | Teller et al. |
| 7,272,982 B2 | 9/2007 | Neuhauser et al. |
| 7,373,820 B1 | 5/2008 | James |
| 7,443,292 B2 | 10/2008 | Jensen et al. |
| 7,457,724 B2 | 11/2008 | Vock et al. |
| 7,505,865 B2 | 3/2009 | Ohkubo et al. |
| 7,653,508 B1 | 1/2010 | Kahn et al. |
| 7,690,556 B1 | 4/2010 | Kahn et al. |
| 7,713,173 B2 | 5/2010 | Shin et al. |
| 7,774,156 B2 | 8/2010 | Niva et al. |
| 7,789,802 B2 | 9/2010 | Lee et al. |
| 7,881,902 B1 | 2/2011 | Kahn et al. |
| 7,927,253 B2 | 4/2011 | Vincent et al. |
| 7,983,876 B2 | 7/2011 | Vock et al. |
| 8,055,469 B2 | 11/2011 | Kulach et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,463,576 B2 | 6/2013 | Yuen et al. |
| 8,463,577 B2 | 6/2013 | Yuen et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,583,402 B2 | 11/2013 | Yuen et al. |
| 2001/0055242 A1 | 12/2001 | Deshmuhk et al. |
| 2002/0013717 A1 | 1/2002 | Ando et al. |
| 2002/0077219 A1 | 6/2002 | Cohen et al. |
| 2002/0082144 A1 | 6/2002 | Pfeffer |
| 2002/0109600 A1 | 8/2002 | Mault et al. |
| 2002/0178060 A1 | 11/2002 | Sheehan |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2004/0054497 A1 | 3/2004 | Kurtz |
| 2004/0117963 A1 | 6/2004 | Schneider |
| 2004/0152957 A1 | 8/2004 | Stivoric et al. |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0228692 A1 | 10/2005 | Hodgdon |
| 2005/0234742 A1 | 10/2005 | Hodgdon |

(56) References Cited

U.S. PATENT DOCUMENTS

| | | |
|---|---|---|
| 2005/0272564 A1 | 12/2005 | Pyles et al. |
| 2006/0020177 A1 | 1/2006 | Seo et al. |
| 2006/0025282 A1 | 2/2006 | Redmann |
| 2006/0047208 A1 | 3/2006 | Yoon |
| 2006/0047447 A1 | 3/2006 | Brady et al. |
| 2006/0089542 A1 | 4/2006 | Sands |
| 2006/0111944 A1 | 5/2006 | Sirmans, Jr. et al. |
| 2006/0129436 A1 | 6/2006 | Short |
| 2006/0143645 A1 | 6/2006 | Vock et al. |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2007/0050715 A1 | 3/2007 | Behar |
| 2007/0051369 A1 | 3/2007 | Choi et al. |
| 2007/0123391 A1 | 5/2007 | Shin et al. |
| 2007/0136093 A1 | 6/2007 | Rankin et al. |
| 2007/0155277 A1 | 7/2007 | Amitai et al. |
| 2007/0179356 A1 | 8/2007 | Wessel |
| 2008/0093838 A1 | 4/2008 | Tropper et al. |
| 2008/0140338 A1 | 6/2008 | No et al. |
| 2009/0018797 A1 | 1/2009 | Kasama et al. |
| 2009/0043531 A1 | 2/2009 | Kahn et al. |
| 2009/0048044 A1 | 2/2009 | Oleson et al. |
| 2009/0171788 A1 | 7/2009 | Tropper et al. |
| 2011/0003665 A1 | 1/2011 | Burton et al. |
| 2011/0009051 A1 | 1/2011 | Khedouri et al. |
| 2011/0022349 A1 | 1/2011 | Stirling et al. |
| 2011/0106449 A1 | 5/2011 | Chowdhary et al. |
| 2011/0131005 A1 | 6/2011 | Ueshima et al. |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0226471 A1 | 9/2012 | Yuen et al. |
| 2012/0226472 A1 | 9/2012 | Yuen et al. |
| 2012/0265480 A1 | 10/2012 | Oshima |
| 2012/0330109 A1 | 12/2012 | Tran |
| 2013/0006718 A1 | 1/2013 | Nielsen et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0096843 A1 | 4/2013 | Yuen et al. |
| 2013/0151196 A1 | 6/2013 | Yuen et al. |
| 2013/0158369 A1 | 6/2013 | Yuen et al. |
| 2013/0231574 A1 | 9/2013 | Tran |
| 2013/0267249 A1 | 10/2013 | Rosenberg |
| 2013/0268236 A1 | 10/2013 | Yuen et al. |
| 2013/0325396 A1 | 12/2013 | Yuen et al. |
| 2014/0039804 A1 | 2/2014 | Park et al. |
| 2014/0039840 A1 | 2/2014 | Yuen et al. |

OTHER PUBLICATIONS

"Classification of Human Moving Patterns Using Air Pressure and Acceleration", Sagawa, et al, Proceedings of the 24th Annual Conference of the IEEE Industrial Electronics Society, vol. 2, Aug.-Sep. 1998, pp. 1214-1219.

"Non-restricted measurement of walking distance", Sagawa, et al, IEEE Int'l Conf. on Systems, Man, and Cybernetics, vol. 3, Oct. 2000, pp. 1847-1852.

"Activity Classification Using Realistic Data From Wearable Sensors", Parkka, et al, IEEE Transactions on Information Technology in Biomedicine, vol. 10, No. 1, Jan. 2006, pp. 119-128.

"Indoor Navigation with MEMS Sensors", Lammel, et al., Proceedings of the Eurosensors XIII conference, vol. 1, No. 1, Sep. 2009, pp. 532-535.

"Design of a Wireless Assisted Pedestrian Dead Reckoning System—The NavMote Experience", Fang, et al, IEEE Transactions on Instrumentation and Measurement, vol. 54, No. 6, Dec. 2005, pp. 2342-2358.

"On Foot Navigation: When GPS alone is not Enough", Ladetto, et al, Journal of Navigation, vol. 53, No. 2, Sep. 2000, pp. 279-285.

"A Hybrid Discriminative/Generative Approach for Modeling Human Activities", Lester, et al., Proc. of the Int'l Joint Conf. Artificial Intelligence, 2005, pp. 766-772.

"Using MS5534 for altimeters and barometers", Intersema App., Note AN501, Jan. 2006.

"Validated caloric expenditure estimation using a single body-worn sensor", Lester, et al, Proc. of the Int'l Conf. on Ubiquitous Computing, 2009, pp. 225-234.

"Drift-free dynamic height sensor using MEMS IMU aided by MEMS pressure sensor", Tanigawa, et al, Workshop on Positioning, Navigation and Communication, Mar. 2008, pp. 191-196.

"Improvement of Walking Speed Prediction by Accelerometry and Altimetry, Validated by Satellite Positioning", Perrin, et al, Medical & Biological Engineering & Computing, vol. 38, 2000, pp. 164-168.

"An Intelligent Multi-Sensor system for Pedestrian Navigation", Retscher, Journal of Global Positioning Systems, vol. 5, No. 1, 2006, pp. 110-118.

"Evaluation of a New Method of Heading Estimation of Pedestrian Dead Reckoning Using Shoe Mounted Sensors", Stirling et al., Journal of Navigation, vol. 58, 2005, pp. 31-45.

"Direct Measurement of Human Movement by Accelerometry", Godfrey, et al., Medical Engineering & Physics, vol. 30, 2008, pp. 1364-1386.

"Foot Mounted Inertia System for Pedestrian Naviation", Godha et al., Measurement Science and Technology, vol. 19, No. 7, May 2008, pp. 1-9.

"Altimeter and Barometer System", Clifford, et al., Freescale Semiconductor Aplication Note AN1979, Rev. 3, Nov. 2006.

"SCP 1000-D01/D11 Pressure Sensor as Barometer and Altimeter", VTI Technologies Application, Jun. 2006, Note 33.

"Suunto LUMI User Guide", Jun. and Sep. 1997.

International Search Report issued on Aug. 15, 2008, in related application PCT/IB07/03617.

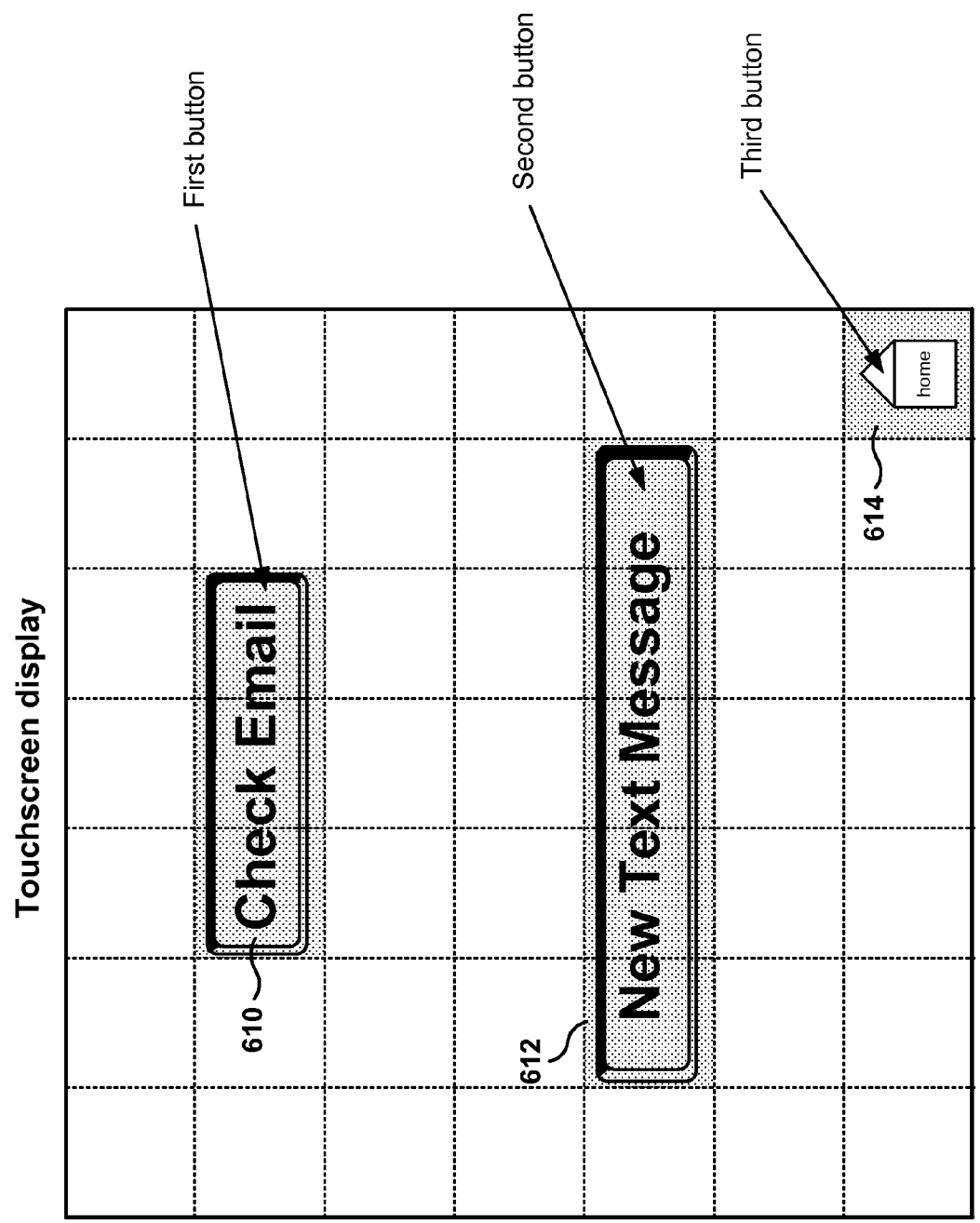

POWER CONSUMPTION MANAGEMENT OF DISPLAY IN PORTABLE DEVICE BASED ON PREDICTION OF USER INPUT

CLAIM OF PRIORITY

This application claims priority from U.S. Provisional Patent Application No. 61/767,932, filed Feb. 22, 2013, and entitled "Dynamic Touch Screen Optimization," which is herein incorporated by reference.

This application is a continuation-in-part of U.S. patent application Ser. No. 13/959,714, filed on Aug. 5, 2013, titled "Methods and Systems for Identification of Event Data Having Combined Activity and Location Information of Portable Monitoring Devices", which is a continuation-in-part of U.S. patent application Ser. No. 13/693,334 (now issued as U.S. Pat. No. 8,548,770, issued on Oct. 1, 2013), filed on Dec. 4, 2012, titled "Portable Monitoring Devices and Methods for Operating Same", which is a divisional of U.S. patent application Ser. No. 13/667,229 (now issued as U.S. Pat. No. 8,437,980, issued on May 7, 2013), filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same", and to U.S. Provisional Patent Application No. 61/390,811, filed on Oct. 7, 2010, and titled "Portable Monitoring Devices and Methods for Operating Same", all of which are hereby incorporated by reference in their entirety.

This application is a continuation-in-part of Ser. No. 13/959,714, filed Aug. 5, 2013, titled "Methods and Systems for Identification of Event Data Having Combined Activity and Location Information of Portable Monitoring Devices", which claims priority to U.S. Provisional Patent Application 61/680,230 filed Aug. 6, 2012, and is a continuation-in-part of U.S. patent application Ser. No. 13/759,485 (now issued as U.S. Pat. No. 8,543,351, issued on Sep. 24, 2013), filed on Feb. 5, 2013, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same" (now issued as U.S. Pat. No. 8,543,351, issued on May 7, 2013), which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

CROSS REFERENCE TO RELATED APPLICATIONS

This application is related by subject matter to U.S. patent application Ser. No. 14/154,123, filed on the same day as the instant application and entitled "Selection of Display Power Mode Based on Sensor Data", and U.S. patent application Ser. No. 14/154,145, filed on the same day as the instant application and entitled "Touchscreen With Dynamically-Defined Areas Having Different Scanning Modes", all of which are incorporated herein by reference.

BACKGROUND

1. Field of the Invention

The present embodiments relate to methods, devices, systems, and computer programs for managing power consumption in a portable device, and more particularly, methods, devices, systems, and computer programs for managing display operation.

2. Description of the Related Art

The use of portable devices has grown exponentially over the last few decades. In order to achieve true portability, portable devices, such as smart phones, tablets, music players, laptop computers, video players, etc., must be operational for acceptable periods of time without the need to recharge the batteries.

One of the components that use a large amount of power in portable devices, oftentimes the most power, is the display. The trend today is towards touch-sensitive displays, also referred to as touchscreens, in order to facilitate user interaction with the portable device. However, the power consumption of touchscreens in electronic devices may significantly affect the overall battery life.

In some portable devices, such as smart phones, the touchscreen is disabled while the user is not utilizing the portable device, and the touchscreen is enabled after the user presses a button on the computing device. This means that the touchscreen does not have to be scanned for touch while the device is not in use. However, some portable devices may not have buttons, and the touchscreen has to be operational at all times. This means that the touchscreen has to be scanned for input continuously, resulting in a potential large consumption of power.

It is in this context that embodiments arise.

SUMMARY

Methods, devices, systems, and computer programs are presented for managing power consumption or processing rates in an activity monitoring device, also referred to herein as a portable device, unless otherwise specified. It should be appreciated that the present embodiments can be implemented in numerous ways, such as a method, an apparatus, a system, a device, or a computer program on a computer readable medium. Several embodiments are described below.

In one embodiment, a method for managing power consumption in a portable device is provided. The method includes an operation for analyzing sensor data acquired by sensors of an activity monitoring device associated with a user, the sensor data being associated with motion of the user. In addition, the method includes an operation for determining the motion profile of the activity monitoring device based on the sensor data. The method further includes an operation for identifying display settings for a display of the activity monitoring device based on the motion profile. The display settings are associated with a rate of power consumption by the display. The display settings are applied to the display of the activity monitoring device when the identified display settings are different than the current display settings. In one embodiment, the operations of the method are executed by a processor.

In another embodiment, one method includes an operation for analyzing sensor data acquired by sensors of an activity monitoring device associated with a user, the sensor data being associated with motion of the user. The method further includes operations for determining the motion profile of the activity monitoring device based on the sensor data, and for identifying display settings for a touchscreen of the activity monitoring device based on the motion profile. The display settings are associated with a rate of power consumption by the display. In addition, the method includes an operation for applying the display settings for the touchscreen when the identified display settings are different than current display settings, where applying the display settings for the touchscreen further includes setting, in a first area of the touchscreen where touch is expected, a first scan rate for detecting touch on the touchscreen; and setting, in a second area of the touchscreen where touch is not expected, a second scan rate. In one embodiment, the operations of the method are executed by a processor.

In another embodiment, a method includes an operation for detecting an event at a portable device. In addition, the method includes operations for examining the event to determine if a notification of the event is predefined to be transmitted to an activity monitoring device, and for transmitting the notification of the event to the activity monitoring device to cause display data to be presented on a screen of the activity monitoring device. In one embodiment, the operations of the method are executed by a processor.

In yet another embodiment, an activity monitoring device includes one or more biometric sensors, one or more motion sensors, a memory, a display, and a processor. The one or more biometric sensors are operable to capture biometric data of a user wearing the activity monitoring device, and the one or more motion sensors are operable to capture motion data. The memory is defined for storing a computer program, biometric sensor data, and motion sensor data. Further, the display has display settings associated with a rate of power consumption by the display. The processor is configured to analyze the motion sensor data, the processor determining a motion profile of the activity monitoring device based on the analyzed motion sensor data, wherein the processor identifies the display settings for the display based on the motion profile, and wherein the processor applies the display settings when the identified display settings are different than current display settings.

In another embodiment, a method includes an operation for setting a first display setting for a touchscreen of an activity monitoring device associated with a user. The first display setting has a first rate of power consumption by the display and a first touchscreen scan rate for detecting touch on the touchscreen. In addition, the method includes operations for receiving data at the activity monitoring device (the data being indicative of an external event), and for applying a second display setting for the touchscreen based on a predefined expected user interaction. The second display setting has a second rate of power consumption and a second touchscreen scan rate. In another embodiment, the operations of the method are executed by a processor.

In yet another embodiment, a method includes an operation for setting a first display setting for a touchscreen of an activity monitoring device to be worn by a user. In addition, the method includes operations for receiving data at the activity monitoring device (the data being indicative of an external event), and for presenting a notification message on the touchscreen regarding the external event. In addition, the method includes an operation for determining if the external event is associated with a predefined expected user interaction with the touchscreen. A second display setting for the touchscreen is applied based on the predefined expected user interaction. Applying the second display setting includes: setting, in a first area of the touchscreen where touch is expected, a first touchscreen scan rate for detecting touch on the touchscreen; and setting, in a second area of the touchscreen where touch is not expected, a second touchscreen scan rate. In one embodiment, the operations of the method are executed by a processor.

Further, in another embodiment, a method includes an operation for setting a first display setting for a touchscreen of an activity monitoring device when the activity monitoring device is not interacting with a user. In addition, the method includes another operation for receiving, at the activity monitoring device, data indicating that the user has received a communication from another user. The method includes another operation for setting a second display setting for the touchscreen, the second display setting including an interface in the touchscreen that enables selection of an option for viewing details of the communication. The interface includes a subregion of the touchscreen for selecting the option for viewing details. Furthermore, setting the second display setting further includes: setting in the subregion a first touchscreen scan rate for detecting touch on the touchscreen; and setting a second touchscreen scan rate in areas of the touchscreen outside the subregion. In one embodiment, the operations of the method are executed by a processor.

In one embodiment, an activity monitoring device includes one or more biometric sensors, a network communications module, a memory, a display with a touchscreen, and a processor. The one or more biometric sensors are for capturing biometric data of a user wearing the activity monitoring device, and the network communications module is for sending and receiving data. The memory is for storing a computer program, biometric data, and communications data. The processor is configured for setting a first display setting for the touchscreen, the first display setting having a first rate of power consumption by the display and a first touchscreen scan rate for detecting touch on the touchscreen. The processor is further configured for applying a second display setting for the touchscreen based on the predefined expected user interaction. The second display setting has a second rate of power consumption and a second touchscreen scan rate.

In another embodiment, a method includes an operation for identifying one or more possible inputs for an activity monitoring device based on a state of the activity monitoring device, the one or more possible inputs being defined to be entered via a touchscreen of the activity monitoring device. Further, the method includes an operation for identifying a first region and a second region in the touchscreen. The first region is associated with the one or more possible inputs, and the second region is defined outside the first region. Further, the method includes operations for establishing in the first region a first touchscreen setting for scanning the first region for touch, and for establishing in the second region a second touchscreen setting for scanning the second region. The first touchscreen setting defines higher processing than the second touchscreen setting. In one embodiment, the operations of the method are executed by a processor.

In yet another embodiment, a method includes an operation for identifying an input expected for the activity monitoring device based on a state of the activity monitoring device, the input being defined to be entered via a touchscreen of the activity monitoring device. The method further includes an operation for identifying a first region and a second region in the touchscreen, the first region being associated with an area of the touchscreen associated with the input, and the second region being defined outside the first region. Further, the method includes operations for establishing in the first region a first touchscreen setting for scanning the first region for touch, and for suppressing scanning for touch in the second region. In one embodiment, the operations of the method are executed by a processor.

In one embodiment, an activity monitoring device includes a step counter, a display with a touchscreen, a memory, and a processor. The memory has a computer program for a display driver that drives the display. In addition, the processor identifies one or more possible inputs to be entered via the touchscreen based on a state of the activity monitoring device, the processor identifying a first region and a second region in the touchscreen, the first region being associated with the one or more possible inputs, the second region being defined outside the first region. In addition, the processor establishes in the first region a first touchscreen setting for scanning the first region for touch, and the processor establishes in the second region a second touchscreen setting for scanning the second region, where the first touchscreen setting defines higher processing than the second touchscreen setting.

In another embodiment, a non-transitory computer-readable storage medium storing a computer program for managing power consumption in an activity monitoring device that is configured to accompany a user is provided. The computer-readable storage medium includes program instructions for identifying one or more possible inputs for an activity monitoring device based on a state of the activity monitoring device, the one or more possible inputs being defined to be entered via a touchscreen of the activity monitoring device. In addition, the storage medium further includes program instructions for identifying a first region and a second region in the touchscreen, the first region being associated with the one or more possible inputs, the second region being defined outside the first region. The storage medium further includes program instructions for establishing in the first region a first touchscreen setting for scanning the first region for touch, and program instructions for establishing in the second region a second touchscreen setting for scanning the second region. The first touchscreen setting defines higher processing than the second touchscreen setting.

Other aspects will become apparent from the following detailed description, taken in conjunction with the accompanying drawings.

BRIEF DESCRIPTION OF THE DRAWINGS

The embodiments may best be understood by reference to the following description taken in conjunction with the accompanying drawings.

FIGS. 6A-6B illustrate a touchscreen with subregions having different scan rates, according to several embodiments.

DETAILED DESCRIPTION

Methods, devices, systems, and computer programs are presented for managing power consumption in an activity monitoring device (AMD), and more specifically for managing the power consumption of a touchscreen in the activity monitoring device. It will be apparent, that the present embodiments may be practiced without some or all of these specific details. In other instances, well known process operations have not been described in detail in order not to unnecessarily obscure the present embodiments.

Figure 1:
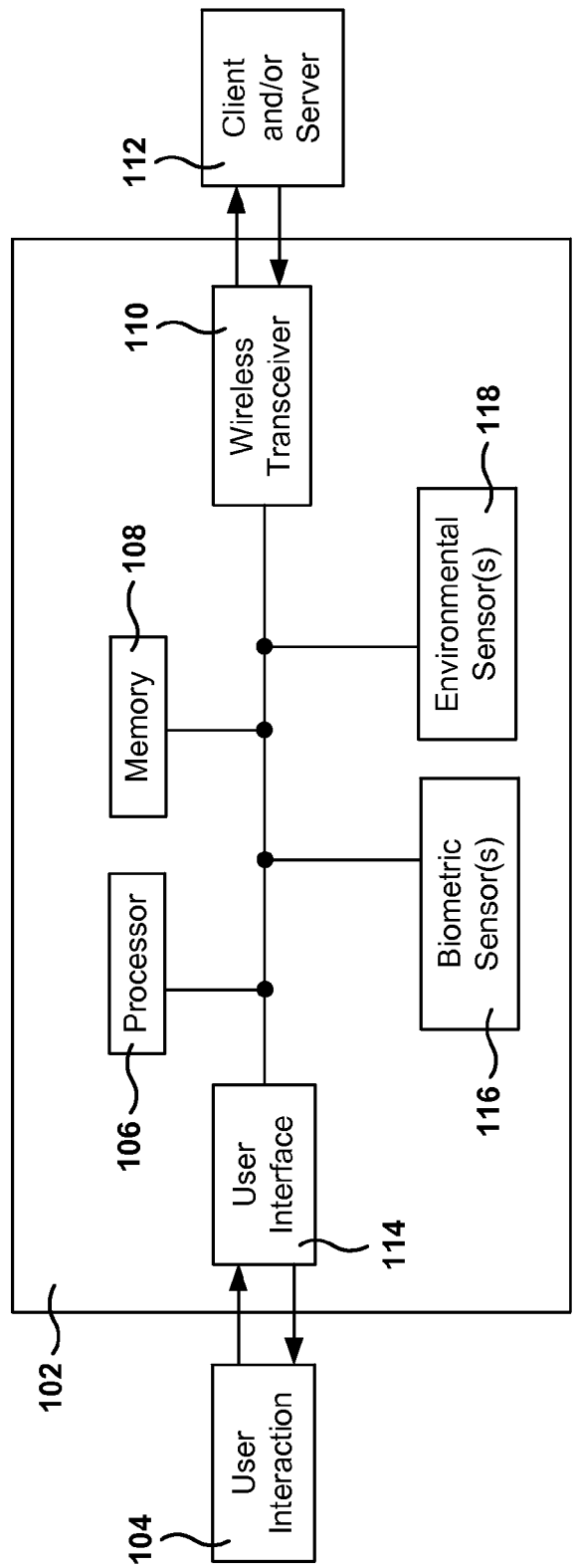
FIG. 1 is a simplified schematic diagram of a computer system for implementing embodiments described herein.

FIG. 1 is a simplified schematic diagram of a computer system for implementing embodiments described herein. In one embodiment, activity monitoring device 102 (also referred to herein as a portable device) includes a processor 106, memory 108, user interface 114, one or more biometric sensors 116, one or more environmental sensors 118, and a wireless transceiver 110.

The processor 106 executes programs for operating the activity monitoring device 102, including power management programs described herein. Memory 108 the stores the computer programs executed by processor 106, although some programs may also be downloaded from an external device, such as a server.

In one embodiment, the user interface 114 manages the interface 104 with the user, and the user interface 114 may include a touchscreen, as described in more detail with reference to FIG. 2, but the user interface 114 may also include buttons, microphones, speakers, connectors (e.g., for a headset), one or more cameras, etc. It is noted that the user may also be able to interface with the device via the biometric sensors, such as by moving the activity monitoring device 102 to form a gesture, tapping the activity monitoring device 102, etc.

Wireless transceiver 110 is used to establish electronic communications with external devices 112, such as another portable device (e.g., smart phone) situated in the vicinity of the activity monitoring device 102, or via network connection to one or more servers.

The activity monitoring device 102 collects one or more types of physiological and/or environmental data from embedded sensors and/or external devices, and communicates or relays such information to other devices or to other internet-viewable sources. In one embodiment, the biometric sensors are used to collect data regarding altitudinal transitions (e.g. climbing stairs) and ambulatory motion (e.g. walking or running). In one embodiment, the device is configured to be worn by a user, and the device monitors certain conditions through one or more sensors, and collects data from the sensors. For example, the device can calculate the user's step count from collected data, store the step count, then subsequently transmit user data representative of the step count to an account on a web service where the user data is stored, processed, and viewed by the user.

The device may monitor, measure, or calculate other physiological metrics in addition to, or in place of, the step count. These metrics include, but are not limited to, energy expenditure, floors climbed or descended, heart rate, heart rate variability, heart rate recovery, location and/or heading (e.g., using global positioning system (GPS) components), elevation, ambulatory speed and/or distance traveled, swimming lap count, bicycle distance and/or speed, blood pressure, blood glucose, skin conduction, skin and/or body temperature, electromyography, electroencephalography, weight, body fat, and respiration rate. The circuitry used to sense and/or calculate these metrics is referred to herein as biometric circuitry.

In one embodiment, activity monitoring device 102 includes environmental sensors 118, which may be used to measure or calculate metrics related to the environment around the user, such as barometric pressure, weather conditions, light exposure, noise exposure, magnetic field, etc.

The activity monitoring device 102 may use one or more of the sensors described below to acquire data, including the data outlined in the tables below. All combinations and permutations of sensors and/or data are intended to fall within the scope of the present embodiments. The electronic device of the present embodiments may include, but is not limited to, some or all the sensors specified below to acquire the corresponding data. Other types of sensors may be employed to acquire the corresponding data, which are intended to fall within the scope of the present embodiments. Additionally, the activity monitoring device may derive the data from the corresponding sensor output data, but is not limited to the number or types of data that it could derive from said sensor. Data acquired from any one or a combination of these sensors may be used to determine the parameters of the touchscreen or for power management.

Table 1 below shows examples of physiological data acquired with respective sensors.

TABLE 1

| Physiological Sensors | Physiological data acquired |
|---|---|
| Optical Reflectometer Potential embodiments: Light emitter and receiver Multi or single LED and photo diode arrangement Wavelength tuned for specific physiological signals Synchronous detection/amplitude modulation | Heart Rate, Heart Rate Variability SpO2 (Saturation of Peripheral Oxygen) Respiration Stress Blood pressure Arterial Stiffness Blood glucose levels Blood volume Heart rate recovery Cardiac health |
| Motion Detector Potential embodiments: Inertial, Gyro or Accelerometer GPS | Activity level detection Sitting/standing detection Fall detection |
| Skin Temp | Stress |
| EMG | Muscle tension |
| EKG Potential Embodiments: 1 lead 2 lead | Heart Rate, Heart Rate Variability, Heart Rate Recovery Stress Cardiac health |
| Magnetometer Laser Doppler Power Meter | Activity level based on rotation |
| Ultra Sound | Blood flow |
| Audio | Heart Rate, Heart Rate Variability, Heart Rate Recovery Laugh detection Respiration Respiration type- snoring, breathing, breathing problems User's voice |
| Strain gauge Potential embodiment: In a wrist band | Heart Rate, Heart Rate Variability Stress |
| Wet sensor Potential embodiment: | Stress Swimming detection |
| Galvanic skin response | Shower detection |

Table 2 below includes a plurality of environmental sensors that may be used to practice embodiments described herein.

TABLE 2

| Environmental Sensors | Environmental data acquired |
|---|---|
| Motion Detector Potential Embodiments: Inertial, Gyro or Accelerometer GPS | Location |
| Pressure/Altimeter sensor | Elevation |
| Ambient Temp | Temperature |
| Light Sensor | Indoor vs. outdoor Watching TV (spectrum/flicker rate detection) Optical data transfer-initiation, QR codes, etc. Ultraviolet light exposure |
| Audio | Indoor vs. Outdoor |
| Compass Potential Embodiments: 3 Axis Compass | Location |

Table 3 below illustrates the derivation of data based on signal processing from multiple sensors.

TABLE 3

| Sensor Integrations | Data derived from signal processing of multiple sensors |
|---|---|
| Skin Temp and Ambient Temp | Heat Flux |
| Heart Rate and Motion | Elevation gain |
| Motion detector and other user's motion detector | Users in the proximity |
| Motion, any heart rate sensor, galvanic skin response | Sit vs. standing detection |

TABLE 3-continued

| Sensor Integrations | Data derived from signal processing of multiple sensors |
|---|---|
| Any heart rate, heart rate variability sensor, respiration, motion | Sleep Phase detection Sleep Apnea detection |
| Any heart rate sensor and/or wetness sensor, and/or motion detector | Resting Heart rate Active Heart Rate Heart rate while asleep Heart rate while sedentary |
| Any heart rate detector | Early detection of heart problems: Cardiac arrhythmia Cardiac arrest |
| Multiple heart rate detectors Audio and/or strain gauge GPS and photoplethysmography (PPG) | Pulse transit time Typing detection Location-stress correlation: Determination of stressful regions Determination of low stress regions Activity specific heart rate Resting heart rate Active heart rate Automatic activity classification and activity heart rate determination |
| Heart rate, galvanic skin response, accelerometer and respiration | User fatigue, for example while exercising |

It is noted that the embodiments illustrated in Tables 1-3 are exemplary. Other embodiments may utilize different sensors, or use these sensors to capture additional data. The embodiments illustrated in Tables 1-3 should therefore not be interpreted to be exclusive or limiting, but rather exemplary or illustrative.

Embodiments modify the characteristics of the touchscreen to manage the power consumption of the screen, such as by lowering power consumption while optimizing the user's interaction with the device (e.g. responsiveness, legibility, etc.) In some embodiments, lower power consumption is the result of using less processing to perform display-related operations than higher power consumption modes. In one embodiment, this feature is achieved by allowing the electronic device to dynamically modify the parameters of the touchscreen based on acquired data or on activities of processes executing in the device.

Contextual information derived from sensors in the device can also aid in touchscreen parameter optimization. Further, by analyzing historical information about a user, habits and trends may be found and used to further alter the parameters of the touchscreen. Embodiments described herein describe some of the touchscreen parameters which may be dynamically changed, and the data which may be used to determine these parameters. The embodiments disclosed herein may be applied to any current touchscreen technology and/or touchscreens yet to be invented including but not limited to capacitive, resistive, surface acoustic wave, surface capacitance, mutual capacitance projected capacitance, self-capacitance projected capacitance, infrared gird, infrared acrylic projection, optical imaging, dispersive signal technology, laser range finding, ultrasound, radar and acoustic pulse recognition, etc.

It is noted that the embodiments illustrated in FIG. 1 are exemplary. Other embodiments may utilize different sensors, additional input mechanisms, additional components or fewer components, etc. The embodiments illustrated in FIG. 1 should therefore not be interpreted to be exclusive or limiting, but rather exemplary or illustrative.

Figure 2:
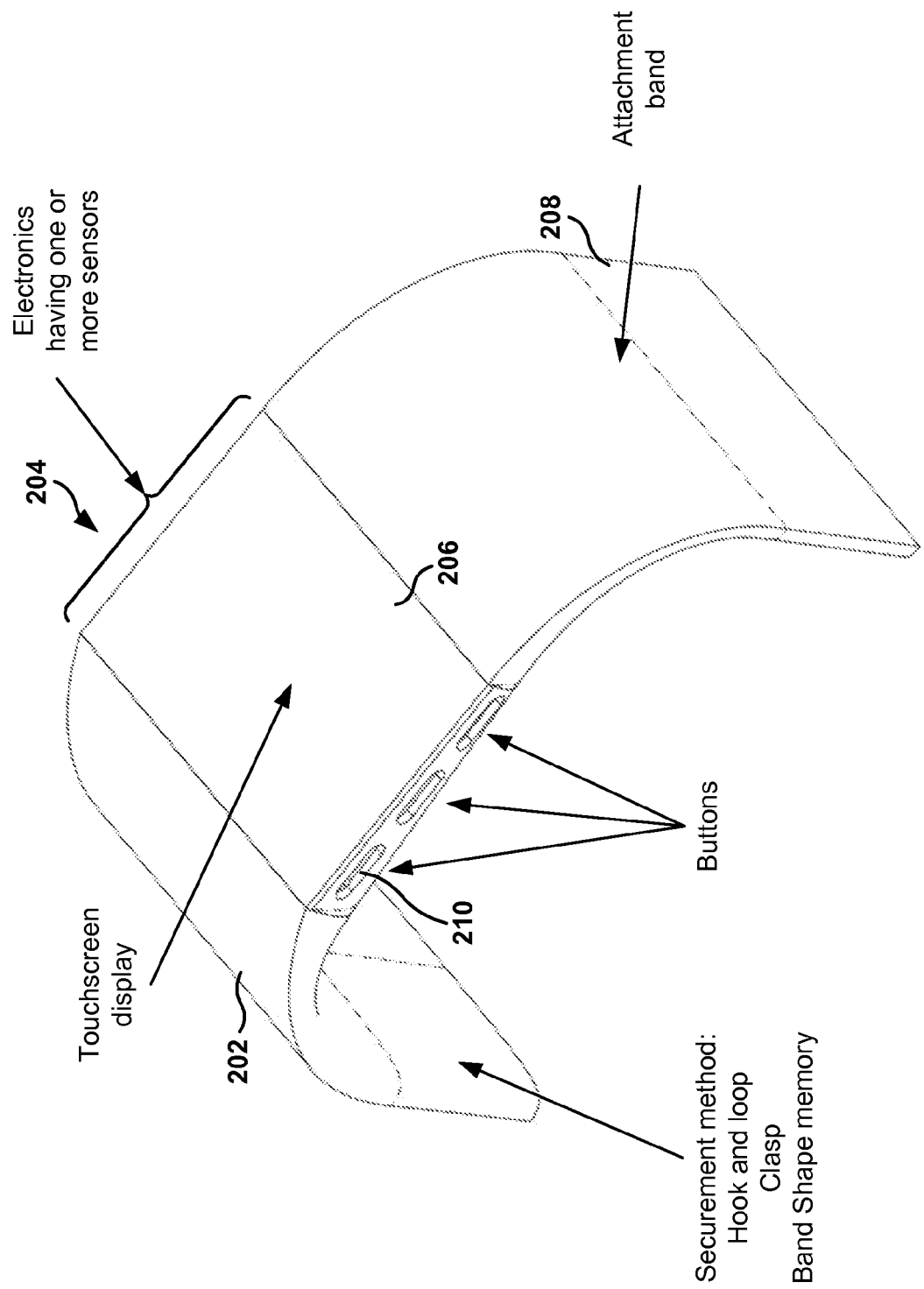
FIG. 2 is a portable biometric monitoring device having a touchscreen, according to one embodiment.

FIG. 2 is an example of a portable biometric monitoring device 202 having a touchscreen 206, according to one embodiment. In one embodiment, the portable biometric monitoring device 202 (also referred to herein simply as the device, or the electronic device, or the portable device) has a shape and size that is adapted to be easily worn about the body of a user, such as by including an attachment band 208 for wearing the device on the wrist. In one embodiment, the portable device 202 includes one or more buttons 210 for user interaction.

In general, the higher the scan rate in a touchscreen, the quicker the touchscreen responds—but a higher scan rate also means that more power is consumed. Embodiments presented herein describe methods for reducing power consumption in touchscreens, while maintaining good response times. In other embodiments, a balance is made to reduce the response time when use conditions do not require the fastest response time, while still providing good performance.

In one exemplary embodiment, the device may decrease its touchscreen's scan rate when it is unlikely for the user to interact with the touchscreen, and increase the scan rate when it is likely for the user to interact with the touchscreen, based on data from its contextual sensors 204, or information from applications or external devices. For example, if the accelerometer detects motion characteristic of running, the device may reduce the scan rate as it is unlikely for the user to interact with the touchscreen during the run. If the user stops running, the scan rate may be increased, as the user is likely wishing to check the device to see running statistics (e.g., how far and how fast the user has run).

For example, a first scan rate may be in a range from 15 to 30 times per second, and the second scan rate may be less than 15 times a second. The ranges of the first scan rate and the second scan rate may vary, as long as one scan rate is slower than the other one, in order to save power during periods of low activity or when the display is not needed. For example, the first scan rate may be in the range of 2 times a second to 15 times a second, or from 10 to 60 times a second, or from 30 to 200 times a second. The second scan rate may range from no scanning at all to 10 times a second, or from 10 to 15 times a second, or from 10 to 60 times a second, etc.

In another embodiment, information from the sensors enables the portable device to determine when the user is sleeping. If the user is detected to be sleeping, one or more of the scan rate, scan area, backlight, or brightness may be reduced, or turned off, as the user is not expected to interact with the touchscreen while sleeping. Therefore, power management is based on the state of activity of the user (as measured by one or more sensors of the device) and a prediction of the behavior of the user based on the state.

In another embodiment, the device includes one or more ambient light sensors. Data from the light sensors may be used, either alone or in combination with other data, to configure one or more operational parameters of the touchscreen. For example, if there is low ambient light and it is nighttime, it may be assumed that the user is sleeping and the scan rate will be decreased.

However, if a significant amount of ambient light is detected, the device may assume that it is daytime, and therefore the user is more likely to interact with the device during the day that at night. To facilitate user input, the device may increase the touchscreen scan rate, contrast, and/or brightness of the display.

In yet another embodiment, an ambient light sensor embedded beneath or near the touchscreen may serve as a proximity detector. When a sudden decrease in light is detected, the scan rate is increased in anticipation of a touch event.

In another embodiment, the device may use one or more sensors to detect gestures made by the user. For example, a watch may know its relative position with regards to the user by monitoring the motion of the watch for a period of time (e.g. five seconds, 60 seconds, although other values are also possible), and determine if the watch is being worn on the right hand, or the left hand. In another embodiment, the user configures, via a user interface (e.g., by login on a server with a web interface), in which hand the user wears the portable device.

These gestures or motions may be indicative of an approaching user interaction, and therefore used to modify parameters of the touchscreen. In one embodiment, where the device is worn on the wrist, the gesture of moving and rotating the wrist in a manner similar to that performed when viewing a watch may cause the touchscreen to increase its scan rate and/or sensitivity.

In some embodiments, the context of the device may be in part or wholly determined by the user instead of being automatically determined. For example, the user may put the device into a specific biometric operating mode such as "sleep tracking" or "running." In one embodiment, the touchscreen's operational parameters are adjusted to reduce the scan rate while in "sleep tracking" mode as the user is unlikely to interact with the device—or if interaction occurs, a quick response is not expected—when the device is in such a mode.

Figure 3:
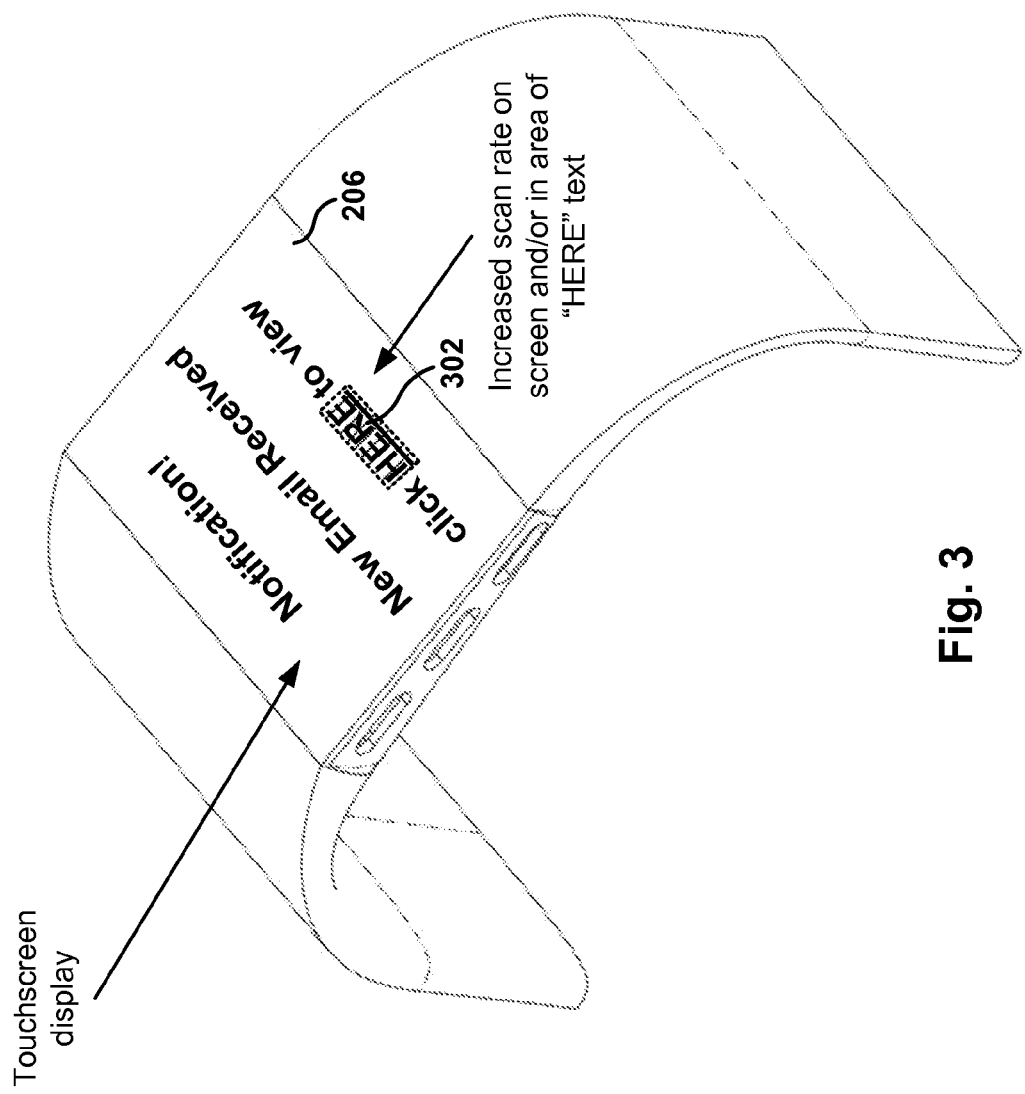
FIG. 3 illustrates a touchscreen with defined areas of higher sensitivity to touch, according to one embodiment.

FIG. 3 illustrates a touchscreen with defined areas of higher sensitivity to touch, according to one embodiment. Touchscreens typically have a rate at which the screen is sampled for touch events. The power consumption of many touchscreens can be dramatically reduced by lowering this scan rate. For example, in some screens, the power consumption of a touchscreen scanning at 20 Hz is nearly three times as high as when the touchscreen scans at 5 Hz.

Some devices, such as smart watches, are turned on most of the time, but users interact with them infrequently. Often, there are short events throughout the day where the user interacts with the device (e.g. to set an alarm). By lowering the scan rate when the user isn't interacting with the device, and by raising the scan rate when the user is interacting with the device, the device feels responsive to the user even though the scan rate is typically low. This way, the average scan rate is lowered significantly, yielding significant power savings. The adjustment of the scan rate in the touchscreen is referred to herein as dynamic scan rate.

It is noted that in some cases, the scan rate may be reduced to zero, effectively turning off the capacity of the touchscreen to detect touches. In some cases, reducing the scan rate can have the beneficial consequence of reducing the number of accidental or false touch detections.

The sensitivity of the touchscreen may be changed dynamically, which is referred to herein as dynamic scan sensitivity. In the case of some touchscreen technologies, a higher sensitivity may enable the touchscreen to detect a touch when the finger has not yet reached the surface of the screen. Configured properly, this sensitivity can be used to predict the approach of a finger to the touchscreen. In one embodiment, when an approach of the finger is detected, the scan rate is increased in anticipation of an upcoming touch event.

Dynamically changing the scan sensitivity enables the electronic device to require that certain touch gestures be performed closer or further away from the display. In one embodiment, the portable device requires a permanent longer touch on the "power off" state to turn off the portable device, therefore reducing accidental power off events.

In another embodiment, by sampling at different levels of sensitivity (e.g., scan rates), the speed of approach of a finger to the screen and the speed of retrieval of the finger away from the screen may be measured. In one embodiment, the approach speed may be mapped to one or more useful characteristics in one or more applications or user interfaces. For example, if the user touches a virtual piano key with a high velocity, a virtual audio reproduction of hitting the virtual piano key hard may be outputted through speakers or headphones.

In the embodiment of FIG. 3, an area 302 of increased sensitivity (e.g., increased scan rate) is defined in touchscreen 206, in response to a notification (e.g., a new mail has been received) presented to the user on the touchscreen. The area 302 of increased sensitivity is where a touch is expected, or sometimes allowed, from the user in response to the notification. In other embodiment, the area of increased sensitivity may be larger or smaller than area 302. For example, in one embodiment, the area of increased sensitivity covers the last line in the notification presented on the touchscreen, so the portable device is responsive to a touch anywhere on the last line.

Additionally, the usability and power consumption of a touchscreen is affected by characteristics other than those used in the detection of touch. These characteristics include, but are not limited to, display brightness, backlight, refresh rate, contrast, gamma, sharpness, and color profile. What is presented on the display and how it is displayed may also change dynamically. For example, the size of icons and/or text may be adjusted to improve legibility depending on the user and/or context of the user. More information regarding a context-dependent user interface is provided in U.S. Provisional patent application No. 61/746,101, which is incorporated by reference in its entirety herein.

It is noted that the embodiments illustrated in FIGS. 2 and 3 are exemplary. Other embodiments may utilize different configurations, size of touchscreens, display of messages, areas of sensitivity, etc. The embodiments illustrated in FIGS. 2 and 3 should therefore not be interpreted to be exclusive or limiting, but rather exemplary or illustrative.

Figure 4:
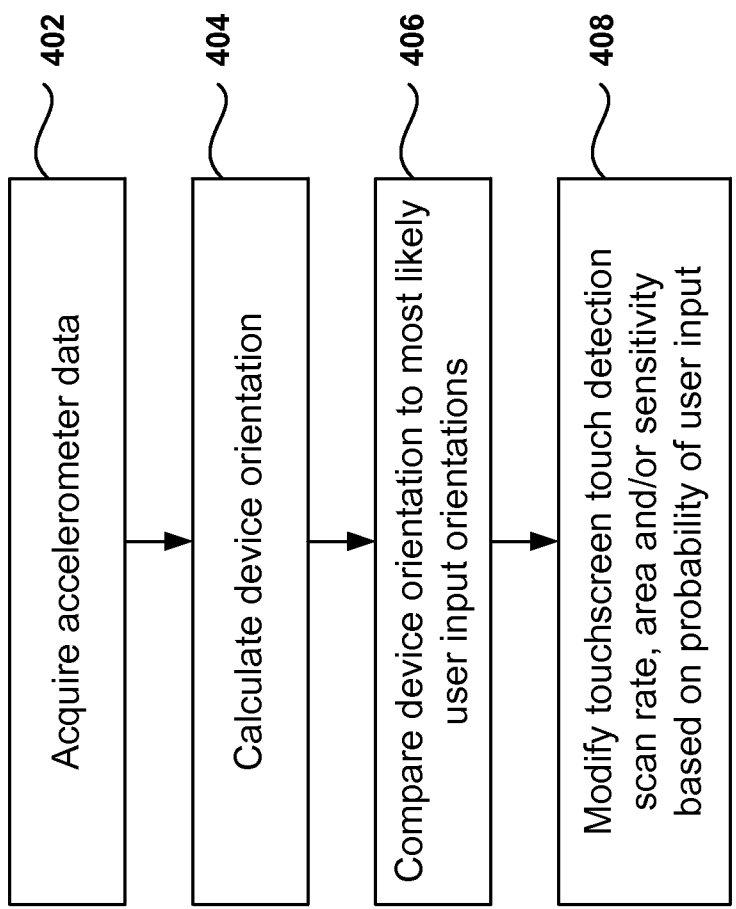
FIG. 4 is a flowchart illustrating a method for optimizing power management for the touchscreen, according to one embodiment.

FIG. 4 is a flowchart illustrating a method for optimizing power management for the touchscreen, according to one embodiment. The electronic device having a touchscreen may use one or more sensors to determine the context of the electronic device. A device state, which is operable to change the parameters of the touchscreen, may be determined based on the device context. One such example of device context is the orientation of the device as determined by one or more accelerometers. In the case of a smart watch device having a touchscreen, it is more likely that the user interfaces with the smart watch when the touchscreen is facing up than when the touchscreen is facing in another direction. Therefore, when the orientation is detected as being up (e.g., based on data acquired from one or more accelerometers) the scan rate and/or the scan area are increased, making the touchscreen more responsive.

In one embodiment, the method for optimizing power consumption in the touchscreen, using orientation information, includes operation 402 where the accelerometer data is acquired by the portable device. From operation 402, the method flows to operation 404 where the device orientation is calculated based on the acquired accelerometer data.

In other embodiments, other environmental and physiological sensors may be used to determine the device orientation. The environmental and physiological sensors include, but are not limited to, altimeters, gyroscopes, galvanic skin response sensors, thermometers, pressure transducers, photoplethysmographs, heart rate sensors, electromyographs, force transducers, strain gauges, magnetometers, humidity sensors, carbon dioxide ($CO_2$) sensors, carbon monoxide (CO) sensors, ambient light sensors, proximity detectors, motion detectors, microphones, sleep detectors, electrocardiographs, etc. It is noted that, in some embodiments, these sensors may be external to the device containing the touchscreen, but in communication with the device (e.g., wirelessly). For example, a heart rate sensor may be connected wirelessly (e.g., Bluetooth, Bluetooth low energy, etc.) to the electronic device.

From operation 404, the method flows to operation 406 where the current device orientation is compared to other device orientations to determine if the current device orientation is likely used for user input. From operation 406, the method flows to operation 408 where one or more parameters for managing power consumption are modified based on the device orientation and/or the probability of receiving user input. The parameters for managing power consumption may include one or more of task screen touch detection scan rate, area in touchscreen defined for touch detection, or touchscreen scan sensitivity.

In one embodiment, the motion history of the portable device is tracked, where the motion history may include one or more positions. The scan rate, or some other power operational parameters, are set based on the motion history of the portable device.

In another embodiment, the position of the portable device is tracked, and the scan rate, or some other power operational parameters, is set based on the current position of the portable device. For example, if the portable device is a watch and the position indicates that the touchscreen is oriented towards the eyes of the user, the power operational parameters are changed to improve response times in case the user interacts with the watch.

In some embodiments, both motion and position are tracked, and the power operational parameters may be adjusted based on both. The motion and position combined may define an activity by the user. For example, the portable device may determine that the user is wearing the portable device and that the user is sleeping, resulting in the touchscreen scan rate being decreased, as no interaction is expected from the user. When the user starts moving, the portable device assumes that the user is now awake and changes the power operational parameters to increase responsiveness in case of interaction with the user.

Other example of activities and/or device state include running or not-running, driving or not-driving, sitting or not-sitting, walking or not-walking, portable device is being worn by the user or not, etc. If the portable device detects that the user has picked up the portable device (e.g., by receiving data from the accelerometer that the portable device is in motion), then the power parameters may be changed as the user is more likely to interact with the device that when the device is not worn.

Figure 5A:
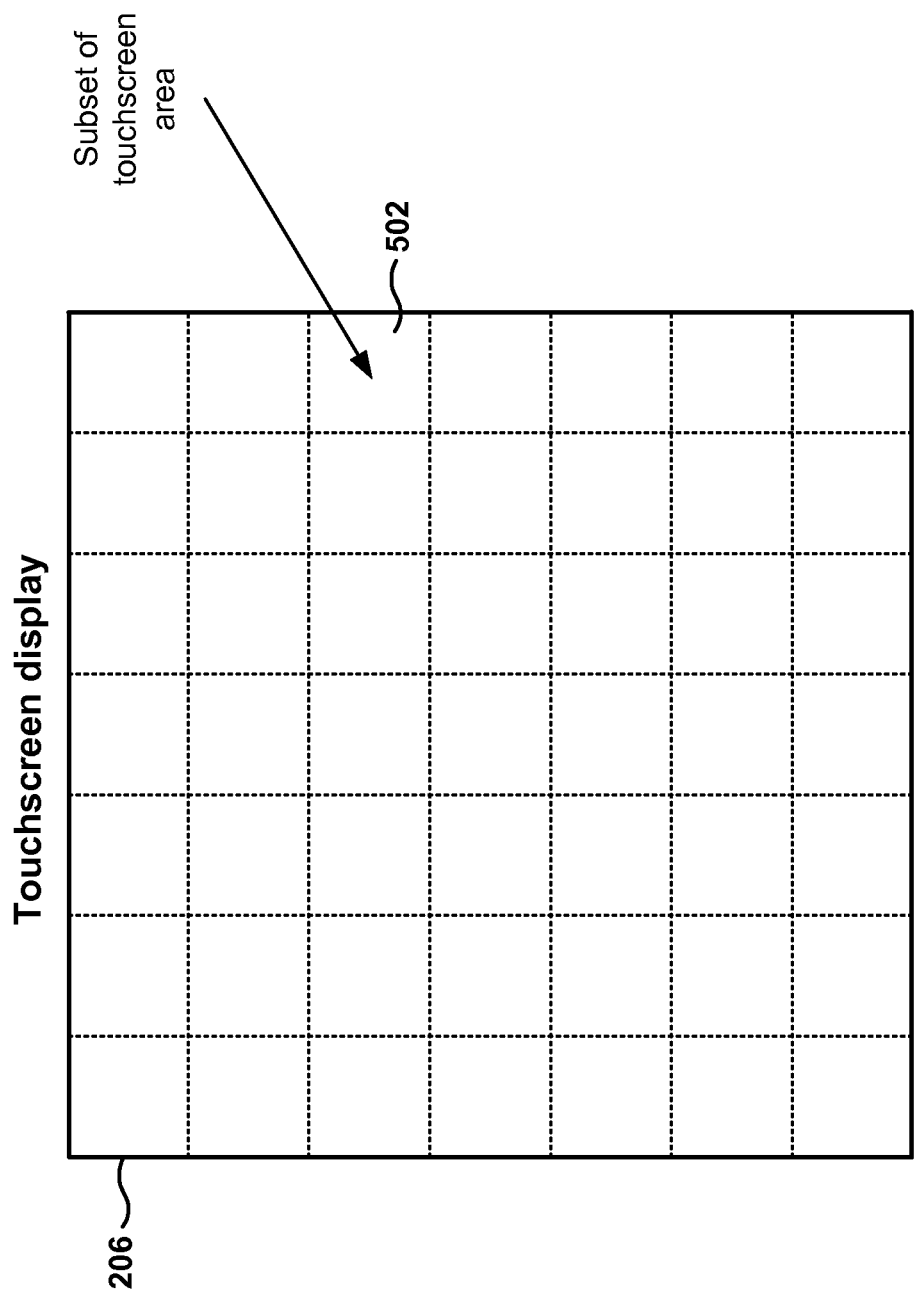
FIGS. 5A-5B illustrate the independent control of subregions in the touchscreen, according to one embodiment.
Figure 5B:
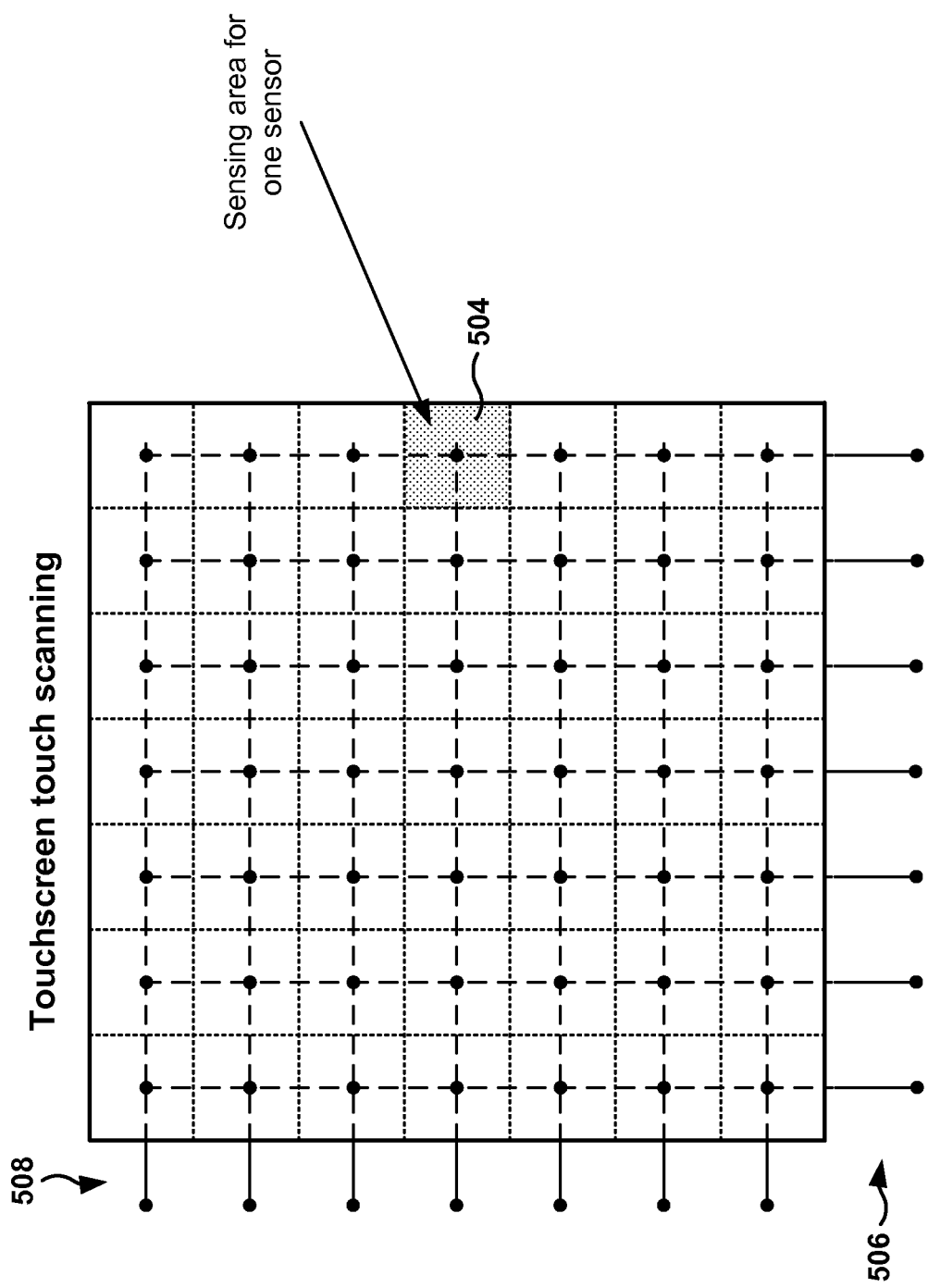

FIGS. 5A-5B illustrate the independent control of subregions in the touchscreen, according to one embodiment. In some touchscreens, specific subsets 502 of the area of the touchscreen, also referred to herein as subregions or cells in the touchscreen, can be controlled independently of other subregions as illustrated in FIG. 5A.

In one embodiment, the touchscreen display is divided in a matrix of cells, where each cell is controlled independently. The independent control means that each cell can have a scan rate that is independently set from the values that are assigned to other cells in the touchscreen.

FIG. 5B illustrates a method for sensing if a touch is taking place in a cell. For description purposes, each cell is said to have an independent sensor. In one embodiment, the touchscreen includes a plurality of horizontal sensing lines 508 and a plurality of vertical sensing lines 506.

In one embodiment, to check for touch or touches in the display, the vertical sensing lines 506 are powered one at a time, and the horizontal sensing lines 508 are "read" one at a time checking for the existence of power. When there is a touch in a cell, a short is made between its horizontal and vertical lines. Therefore, if the corresponding vertical line is powered and there is a touch, the power or voltage will extend into the corresponding horizontal line. In another embodiment, the horizontal sensing lines 508 are powered and the vertical lines 506 are used for reading and detecting if there has been a touch.

In this embodiment, each of the intersections (e.g., cell) is red independently, but in other embodiments groups of cells may be sensed at the same time if the program driving the touchscreen needs to know only if there has been a touch in any of the cells in the group, without specificity to which cell of the group has been touched. More examples are described below for multiple-cell detection in FIGS. 9A-9B.

It is noted that the embodiments illustrated in FIGS. 5A-5B are exemplary. Other embodiments may utilize different number of rows and columns in the display. The embodiments illustrated in FIGS. 5A-5B should therefore not be interpreted to be exclusive or limiting, but rather exemplary or illustrative.

Figure 6A:
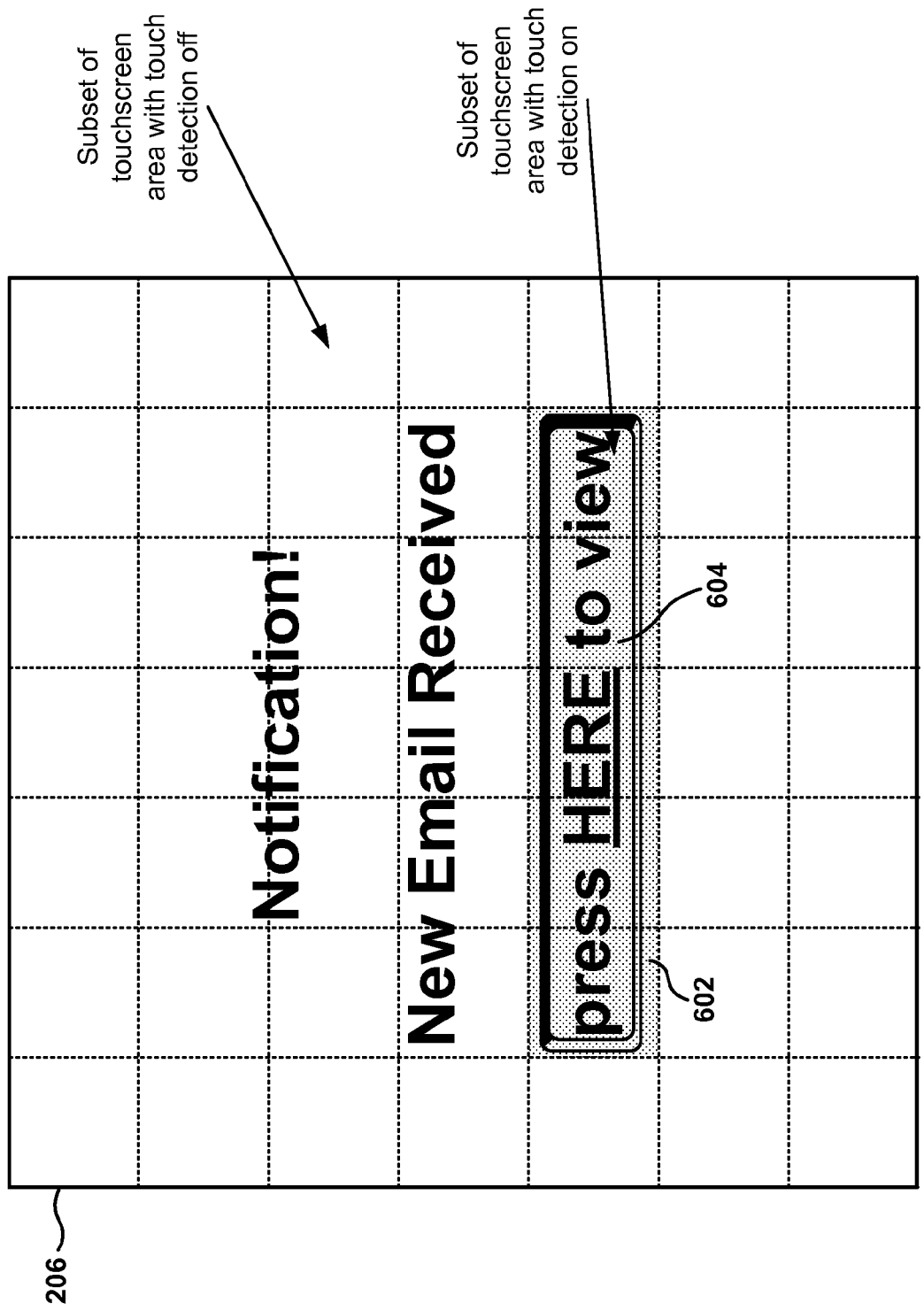

FIGS. 6A-6B illustrate a touchscreen with subregions having different scan rates, according to several embodiments. In one embodiment, the different cells in the touchscreen may have different scan rates varying from zero (cell OFF) to the highest scan rate possible for the screen.

In one embodiment, scan rates are adjusted based on how quickly the user expects a response. In other words, the scan rate may be adjusted based on user expectations or expected user behavior. For example, if the user interface includes the possibility of entering a "flick" gesture, this gesture requires a fast response from the touchscreen because the flick usually takes place quickly. For example, if the touchscreen is scanned five times a second, the user interface may miss the input of a fast flick gesture.

In the embodiment of FIG. 6A, a notification message has been presented to the user on the display. The last line of the message provides a shortcut for the user to access a program in the portable device (e.g., email). In one embodiment, a button 604 is defined on the screen for accessing the program. In addition, a plurality of cells 602 in the screen are scanned for presence of touch, while other areas outside the plurality of cells 602 are not scanned (i.e., turned OFF), or scanned at a lower frequency. The button 604 is displayed on the portion of the screen 602 to indicate that this area of the screen is where the input is expected.

As most of the screen is not scanned, the experience to the user is identical to having the whole screen scanned, even though the scan rate is lower or OFF for certain parts of the screen. By a scanning a subset of the touchscreen, significant power savings are achieved.

FIG. 6B illustrates a touchscreen with several "hot" areas, where a hot area is an area in the display that is being scanned for input. The portable device scans hot areas 610, 612, and 614 for touch, while ignoring the rest of the touchscreen. The graphic user interface has defined three buttons for user input: the first button in area 610 provides a shortcut to open the email application, the second button in area 612 provides a shortcut for reading a new text message, and the third button in area 614 provides a shortcut to go to the home screen.

Areas 610 and 612 encompass a plurality of cells, while area 614 includes only one cell. By limiting the number of cells of the touchscreen that are being scanned, power savings are achieved.

Figure 6C:
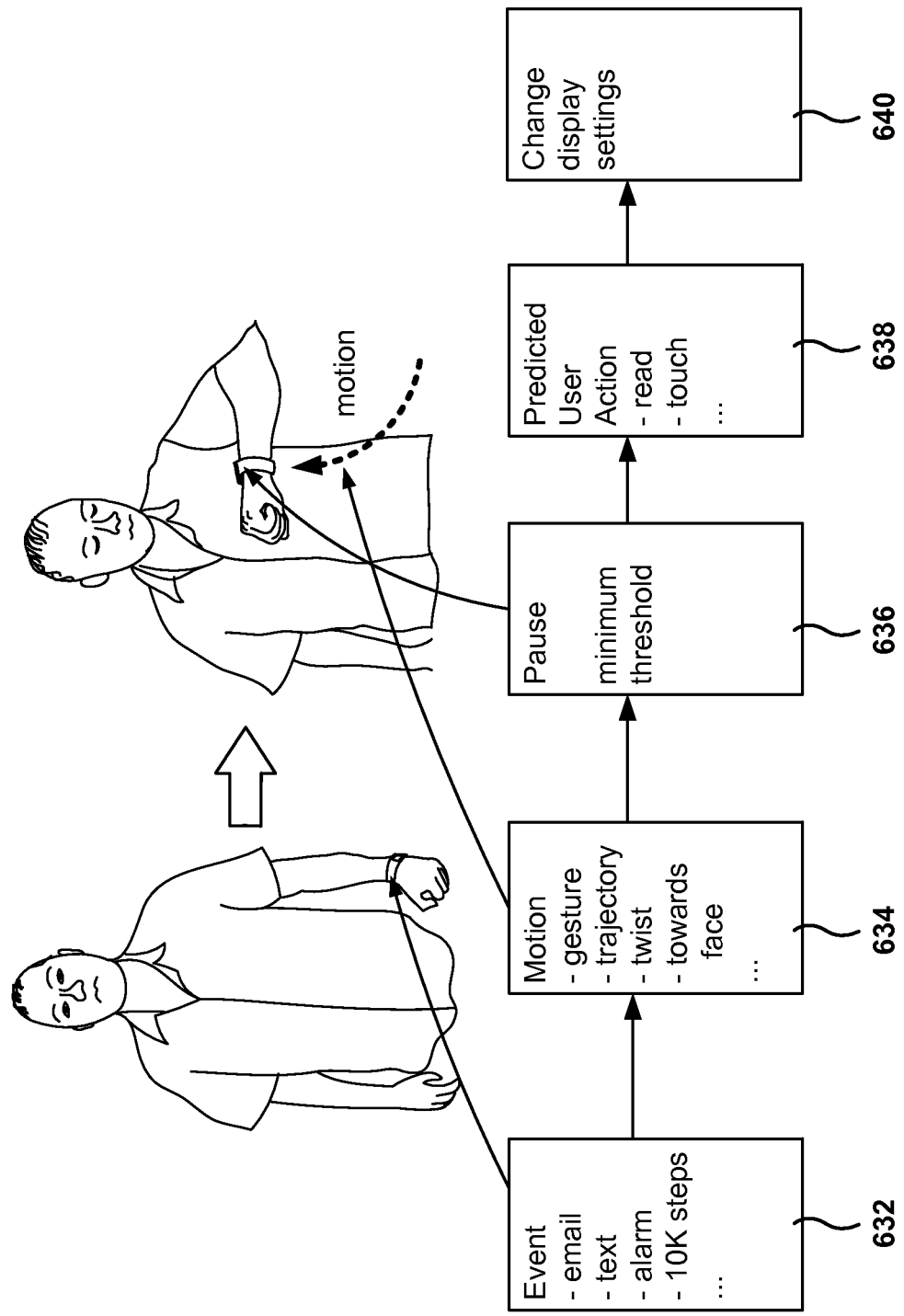
FIG. 6C illustrate the change of display settings in response to user motion, according to one embodiment.

FIG. 6C illustrate the change of display settings in response to user motion, according to one embodiment. In one embodiment, the portable device detects events and motion profiles to determine when to change the display settings. The motion profile may include one or more periods when the device is in motion, as well as one more periods when the device is not in motion (i.e., substantially static), (e.g., a pause while the user is predicted to be looking at the display on the portable device).

In addition, certain motion profiles are activated after the device is in motion and ends in a predetermined position or state, which may also include a predetermined pause. However, there may be several motions that end up in a certain position of the portable device and the trajectory on how the portable device reached that position may not be important. For example, there might be several trajectories for the portable device to place the portable device in front of the eyes of the user (e.g., the display is oriented toward a face of the user), to read the time for example. Accordingly, the portable device predicts that the user is looking at the display and may change the display settings accordingly, without requiring a predetermined trajectory. In this embodiment, the determining factor is that there has been a motion (any motion) that terminates with the display oriented toward the eyes of the user.

In the embodiment shown in FIG. 6C, an event 632 is detected by the portable device. The event may be externally originated (e.g., text message received on a smart phone) when the event is originated or detected in a device other than the portable device, or the event may be internally generated (e.g., the user has reached a goal of walking 10,000 steps) when the event is originated or detected by the portable device.

After receiving the event, the portable device detects a motion 634 that the portable device associates with the received event, that is, the motion is responsive to the event. The motion may include a gesture, a trajectory, a twist of the portable device, moving the portable device so the display is facing the user, etc.

After the motion, the portable device determines a pause 636. In one embodiment, the pause is determined when the portable device stays stationary for at least a predetermined amount of time (e.g., two seconds, although other values are also possible.

After detecting the event, the motion, and the pause, the portable device determines a predicted interaction of the user with the portable device. For example, the user may select a button on the portable device, or tap the portable device. Because input on the touchscreen is predicted, the portable device changes the display settings to improve accuracy for the expected touch input. For example, the portable device may increase the scan rate for better determining a possible touch gesture on the touchscreen.

It is noted that the embodiments illustrated in FIG. 6C are exemplary. Other embodiments may utilize only motion and pause to change the display settings, or consider additional environmental variables (e.g., time of day, user is driving, etc.), or any other combination thereof, etc. The embodiments illustrated in FIG. 6C should therefore not be interpreted to be exclusive or limiting, but rather exemplary or illustrative.

Figure 7A:
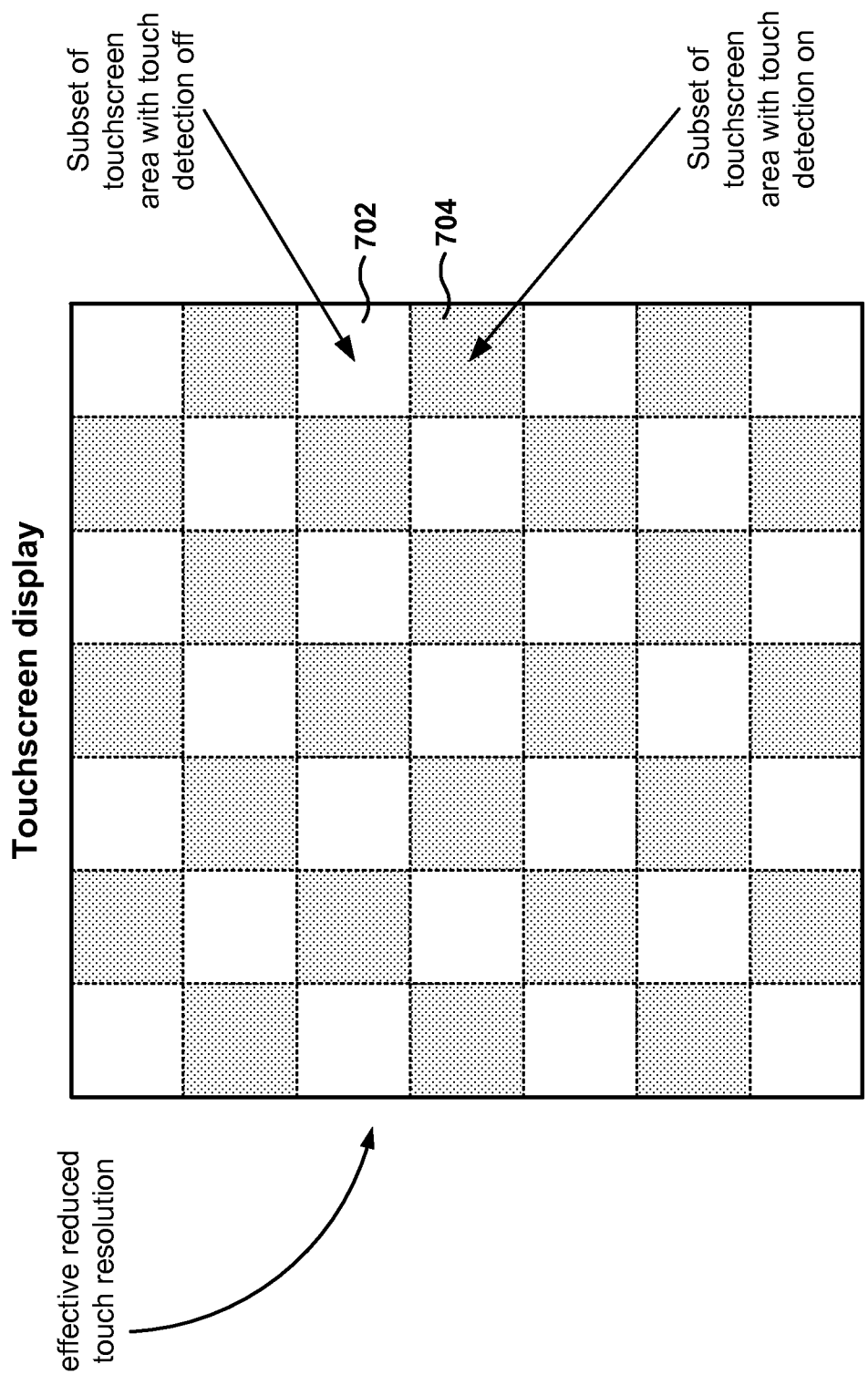
FIGS. 7A-7C illustrates the definition of touchscreen subregions with different scan rates, according to several embodiments.
Figure 7C:
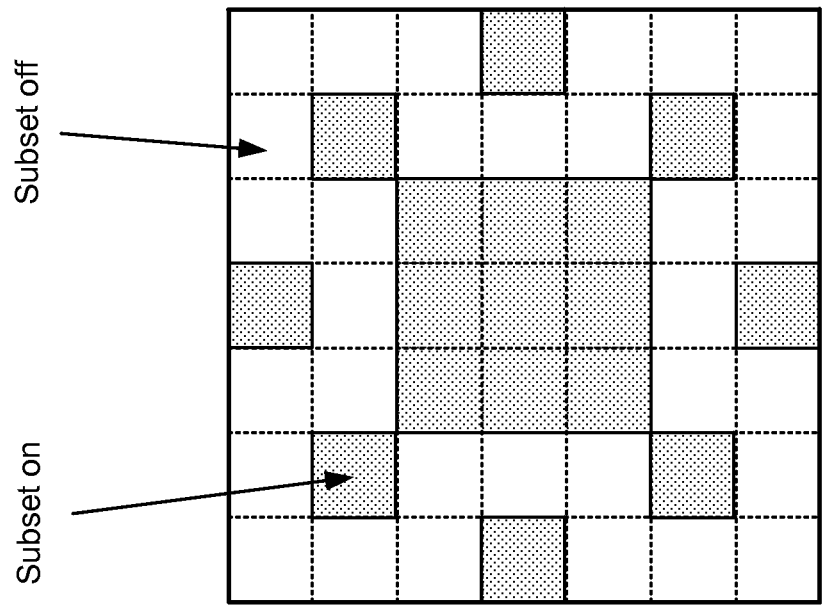
Figure 7B:
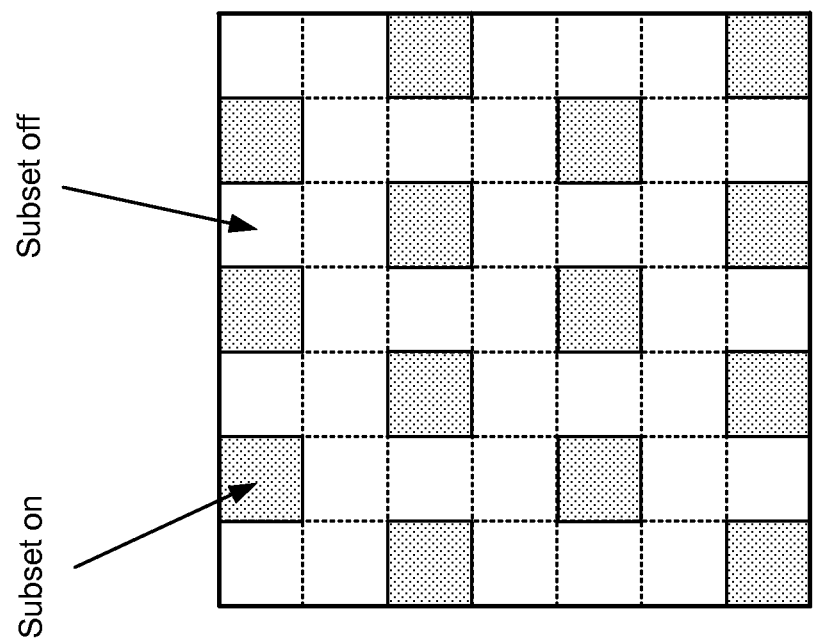

FIGS. 7A-7C illustrates the definition of touchscreen subregions with different scan rates, according to several embodiments. By not scanning or reducing scanning on every other scan area subset, as illustrated in FIG. 7A, the resolution of scanning can be decreased. In some cases, reducing the scan area can reduce the number of accidental or false touch detections. The exemplary embodiment of FIG. 7A defines a checkerboard pattern on the display, where some cells 704 have touch detection ON, while other cells 702 have touch detection OFF.

By scanning half of the cells, power consumption due to touchscreen scanning is reduced in half. This configuration allows the quick detection of a first touch (e.g., a swipe from left to right or from top to bottom) because the expected touch gesture will include at least one of the cells being scanned.

In one embodiment, after detecting the first touch, the display may change the scanning parameters. For example, the display may start scanning the complete screen, or some other subsets of the screen such as the one described in FIGS. 6A and 6B.

FIG. 7B illustrates a different pattern of cells ON and OFF. This pattern is useful, for example, when a diagonal touch gesture is expected. FIG. 7C illustrates a pattern with a high concentration of cells ON in the center, and less density of cells ON in the periphery of the display. This configuration is useful when a touch is expected near the center of the display.

In some graphical user interfaces, a portable device is locked until the user enters a predefined gesture password, which is entered via touch. The touch my includes one or more touches, slides, pinches, etc. In one embodiment (not shown), the user interface determines which cells are turned ON or OFF based on the expected login gesture password. In one embodiment, after the portable device detects that the user is entering the password, the touchscreen is changed to full resolution in order to determine the correct entry of the password.

It is noted that the embodiments illustrated in FIGS. 7A-7C are exemplary. Other embodiments may utilize different scan regions, different number of cells, different number of cells scanned, etc. The embodiments illustrated in FIGS. 7A-7C should therefore not be interpreted to be exclusive or limiting, but rather exemplary or illustrative.

Figure 8:
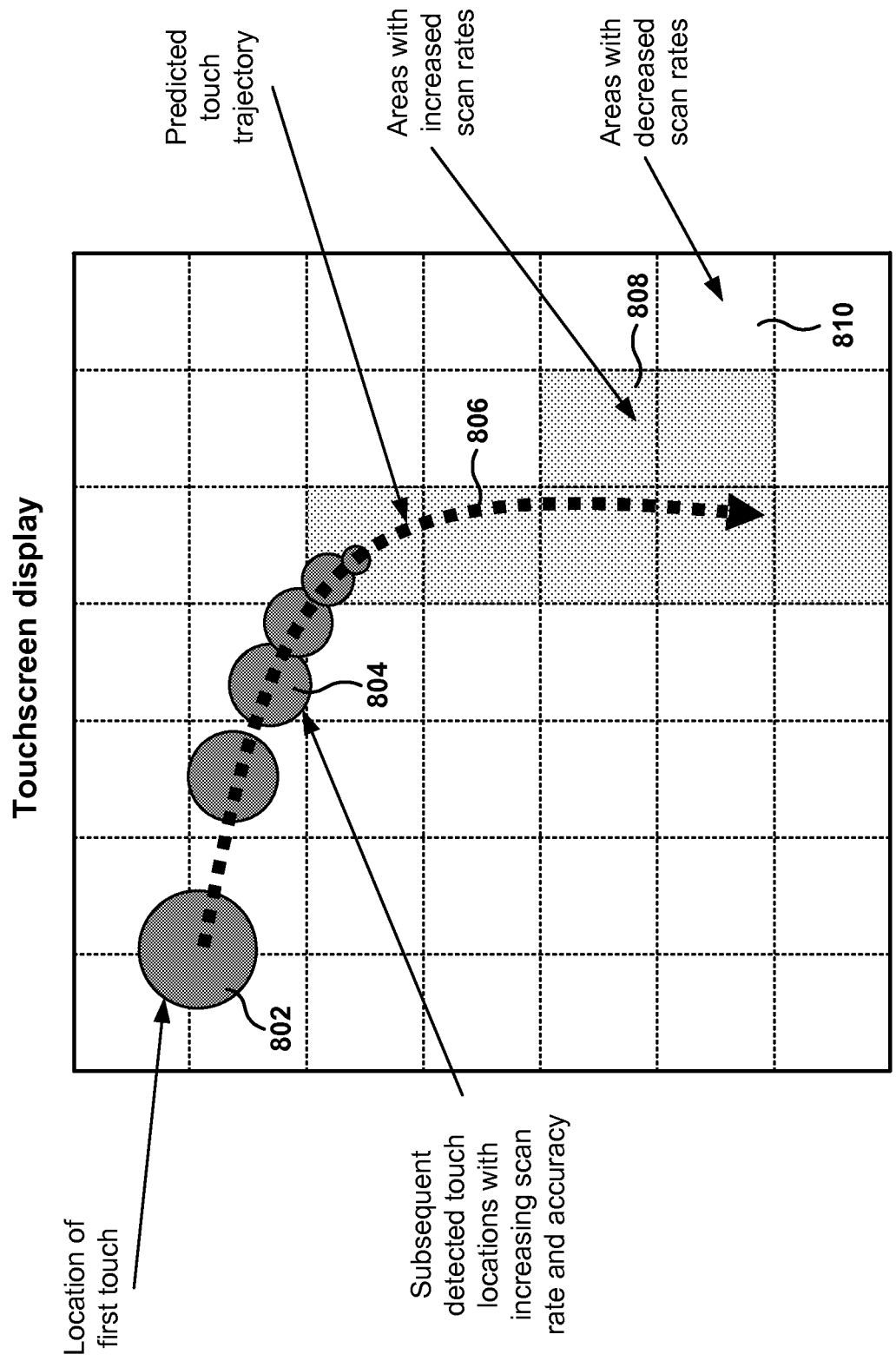
FIG. 8 illustrates a method for adjusting subregion scan rates based on a predicted trajectory of a touch, according to one embodiment.

FIG. 8 illustrates a method for adjusting subregion scan rates based on a predicted trajectory of a touch, according to one embodiment. In one embodiment, the speed and trajectory of the user's touch is used to determine which areas are scanned, and the rate at which the areas are scanned. For example, the first few points where a user touches 802 and 804 are used to predict the trajectory 806 of future touches.

As a result, area 808 where the touch is projected to happen is activated or have the scan rate increase. The speed with which the touch is predicted to go through those areas can also be used to determine the scan rate. Other areas 810 which are not expected to be touched may have decreased scan rates.

In one embodiment, the touchscreen is initially set at a low scan rate and low resolution, so the location of the first touch 802 is determined with low accuracy. After the first touch is detected, the scan rate is increased in order to better determine the trajectory of the touch gesture. Therefore, as time goes by, the accuracy of the touch is increased.

In one embodiment, the electronic device may store and/or analyze previous user interactions and behaviors to predict when and how the user is likely to interact with the touchscreen. Behaviors may be monitored, analyzed, and used to determine operational parameters for the touchscreen. Monitored characteristics of these behaviors may include one or more of the following behaviors described below in Table 4.

TABLE 4

Behavior monitored

What gesture the user usually performs when touching the touchscreen for the first, second, and nth time, where n is a number larger than three. For each gesture, the device may determine one or more of where the gesture begins, the speed of the gesture, the length of the gesture, the trajectory of the gesture, etc.

How quickly, accurately, and/or precisely the user interacts with the touchscreen.

What time of day, week, month, and/or year the user usually interacts with the device. In one embodiment, this includes what type of interaction is performed at what time of day, week, month and/or year.

In what geographical location the user is located when interacting with the device. In what geographical location the user is most likely to be located when interacting with the portable device.

How many stimulants (e.g. coffee) the user has consumed in the last day, week and/or month.

How much sleep the user has gotten in the last night, day, week, month, or any other type of predetermined time period.

How active the user has been in the last minute, hour, day week, month, or any other type of predetermined time period.

How many times the user has pressed snooze on the alarm clock.

How a physiological measure of the user has changed (e.g. is the heart rate higher than usual).

How an environmental measure of the user has changed (e.g. is the user in a new location?).

How long ago since the last interaction between the user and the device occurred.

Physical gestures that the user performs (e.g. by moving the hand or rotating the wrist).

---

Also, historical use data from other users may be analyzed by the servers to construct prediction profiles. The prediction profiles can be used initially when the user is new to the device. The prediction profiles may be templates, which may be assigned to users based on their profile. Over time, the assigned profiles can be fine tuned or adjusted based on the user's actual use or activity.

In some embodiments, one or more behaviors are analyzed together to deduce complex behaviors, also referred to as compound behaviors or long-term behaviors. For example, the geographical location and the time of day that a user normally interacts with the device may be used together to better predict when the user is likely to interact with the touchscreen.

In some embodiments, the characteristics of how the user interacts with the touchscreen may be used to infer various physiological characteristics. For example, if a user interacts with the touchscreen slowly and inaccurately, it may be inferred that the user is drowsy. In some embodiments, data about how the user interacts with the touchscreen is used along with data from other sensors to infer a physiological or environmental state.

In some embodiments, the device has a calibration mode where the device analyzes sensor data to obtain a baseline for typical user behavior. For example, upon the first day that the user uses the device, the device may have a high scan rate all day long. With the data from the first day, the device may reduce the scan rate when it is unlikely for the user to interact with the device. This calibration event may occur at different regular intervals, such as hourly, daily, weekly, monthly, quarterly, annually, etc.

It is noted that all combinations of internal device states and/events, contextual device states, and/or predictive user interactions are intended in the scope of the present embodiments to be used alone or together to optimize touchscreen parameters disclosed herein.

Figure 9A:
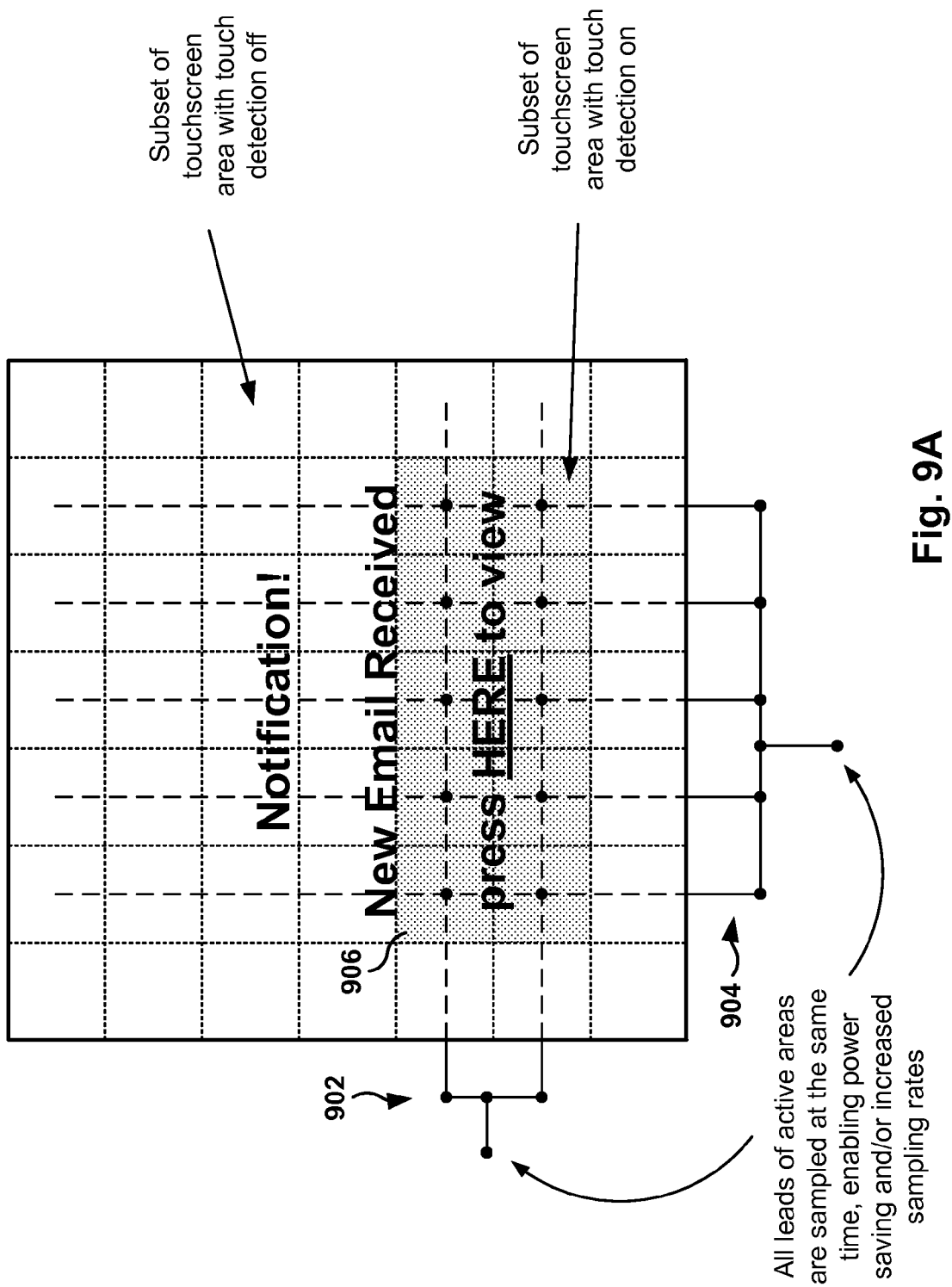
FIGS. 9A-9B illustrate the simultaneous scanning for touch in several cells within the touchscreen, according to several embodiments.
Figure 9B:
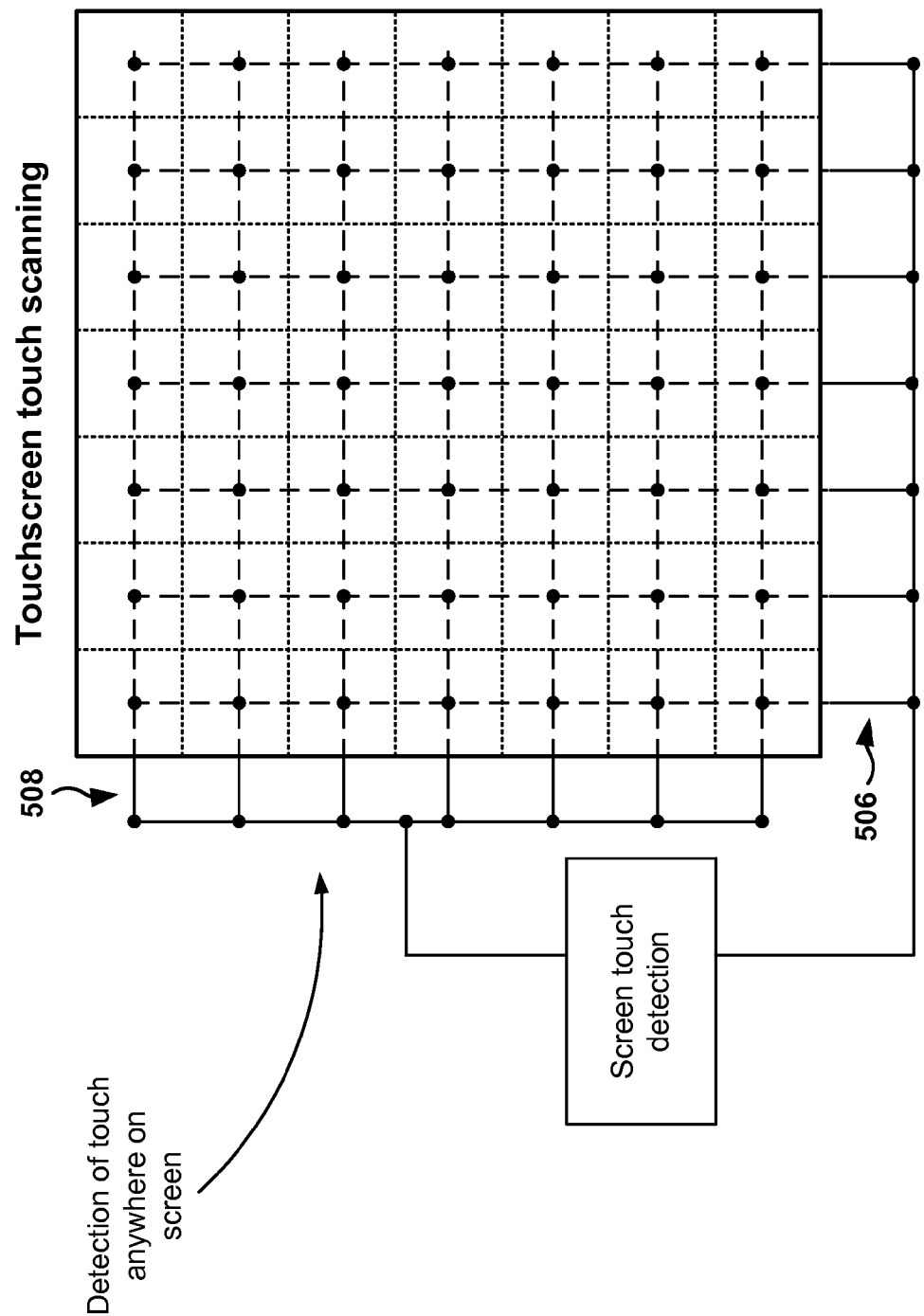

FIGS. 9A-9B illustrate the simultaneous scanning for touch in several cells within the touchscreen, according to several embodiments. As discussed above, the scan rate may be changed in different areas of the display according to a predicted potential input by the user.

In one embodiment, instead of scanning one cell of the display at a time, as described above with reference to FIG. 5B, a group of cells are scanned together to detect a touch in the area encompassed by the plurality of cells.

In one embodiment, the scan lines are not scanned independently; instead some the scan lines may be connected together to be scanned simultaneously. Alternatively, the lines are not connected together but they are powered at the same time, which produces the same effect as if the lines were coupled together. In other words, the touchscreen may be segmented into one or more different areas, where each of the areas has different scan rates, or scan rates that are independent from other areas. The scan rate in one segment may be set independently from the scan rate in other segment of the touchscreen.

In the embodiment of FIG. 9A, a "hot area" is defined around the place where a touch is expected. In this example, the hot area 906 is defined around the message "press HERE to view," because this is the area where the touch of the user is expected.

To scan area 906, the vertical lines 904 associated with the cells in this hot area are also connected together. In another embodiment, the vertical lines are not connected together but they are read at the same time. Similarly, the horizontal lines 902 associated with the cells in the hot area are also connected together. The whole area 906 is scanned in one operation by powering vertical lines 904 together and then checking horizontal lines 902 to detect for power. If power is detected, one or more of the cells in area 906 have been touched, causing the closing of the corresponding switch or switches, which would cause the power to propagate to the horizontal lines 902 that are read for a potential touch.

In the embodiment of FIG. 9B, the whole touchscreen is scanned at the same time. That is, the whole screen defines a single touch area. In the embodiment of FIG. 9B, the vertical lines 506 have been coupled together and the horizontal lines 508 have been coupled together. In another embodiment, the lines are not coupled together but they are powered or read at the same time. The screen touch detection module powers the vertical lines 506 at the same time and reads the single feedback line from horizontal lines 508. As discussed above, if any cell in the touchscreen is touched, the short in the cell caused by the touch closes the circuit and a positive touch read takes place.

In this case, the resolution of the screen has changed from n×m (e.g., 7×7 in the example of FIG. 9A) to 1×1. As a result, power consumption is decreased because the electronic device only scans one area, and the scan rate may be decreased.

It is noted that the embodiments illustrated in FIGS. 9A-9B are exemplary. Other embodiments may utilize different touch areas, or connect the horizontal and vertical lines in different configurations. The embodiments illustrated in FIGS. 9A-9B should therefore not be interpreted to be exclusive or limiting, but rather exemplary or illustrative.

Figure 10:
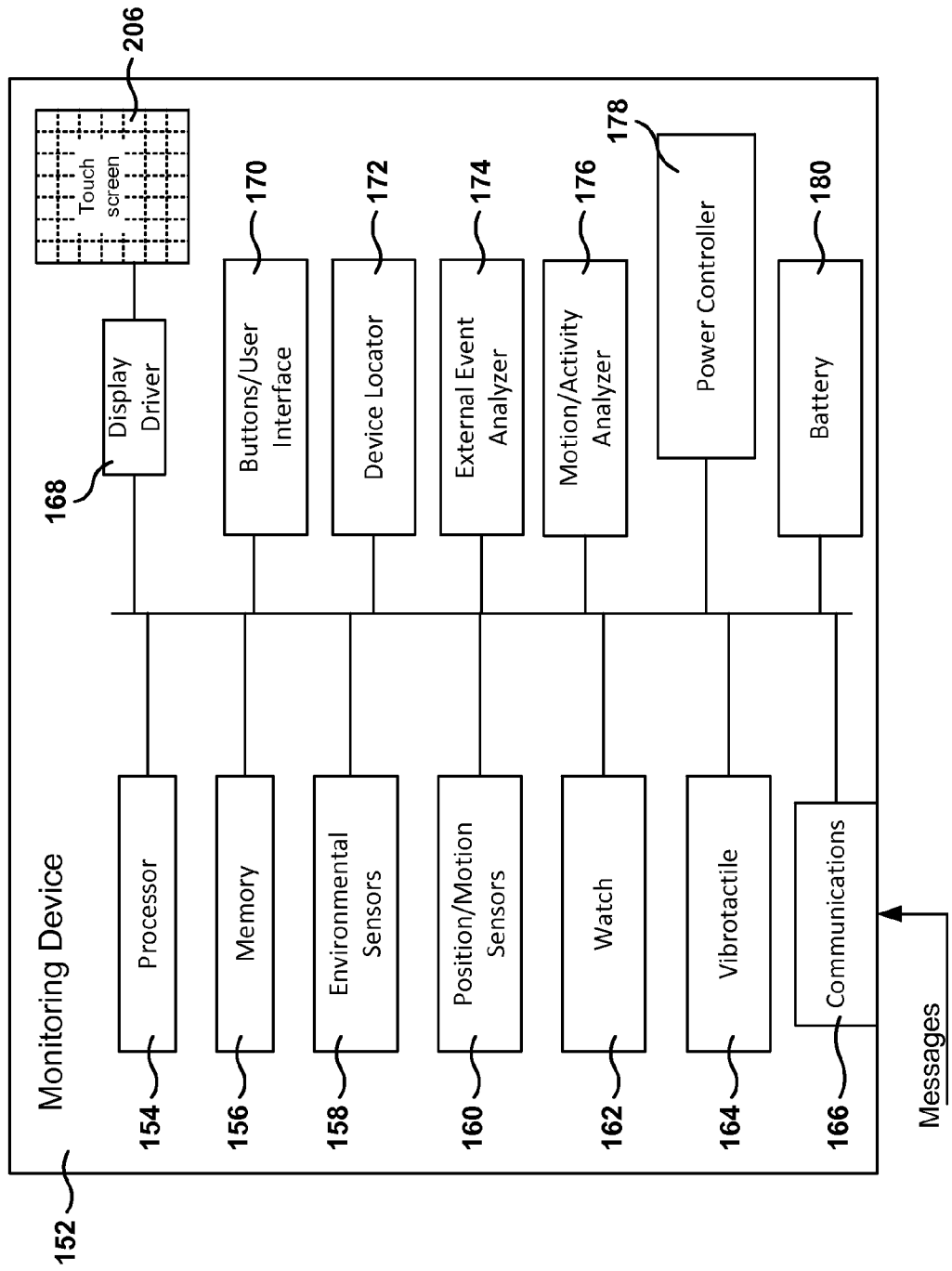
FIG. 10 is a simplified schematic diagram of a device for implementing embodiments described herein.

FIG. 10 is a simplified schematic diagram of a device for implementing embodiments described herein. The monitoring device 152 is an example of any of the monitoring devices of FIGS. 2 and 3, but it could also be another type of devices, such as a fitness tracker without buttons, or a fitness tracker defined to be clipped onto the belt of a user, etc. The monitoring device 152 includes processor 154, memory 156, one or more environmental sensors 158, one or more position and motion sensors 160, watch 162, vibrotactile feedback module 164, display driver 168, touchscreen 206, user interface/buttons 170, device locator 172, external event analyzer 174, motion/activity analyzer 176, power controller 178, and battery 180, all of which may be coupled to all or some of the other elements within monitoring device 152.

Examples of environmental sensors 158 include a barometric pressure sensor, a weather condition sensor, a light exposure sensor, a noise exposure sensor, a radiation exposure sensor, and a magnetic field sensor. Examples of a weather condition sensor include sensors for measuring temperature, humidity, pollen count, air quality, rain conditions, snow conditions, wind speed, or any combination thereof, etc. Examples of light exposure sensors include sensors for ambient light exposure, ultraviolet (UV) light exposure, or a combination thereof, etc. Examples of air quality sensors include sensors for measuring particulate counts for particles of different sizes, level of carbon dioxide in the air, level of carbon monoxide in the air, level of methane in the air, level of other volatile organic compounds in the air, or any combination thereof.

Examples of the position/motion sensor 160 include an accelerometer, a gyroscope, a rotary encoder, a calorie measurement sensor, a heat measurement sensor, a moisture measurement sensor, a displacement sensor, an ultrasonic sensor, a pedometer, an altimeter, a linear position sensor, an angular position sensor, a multi-axis position sensor, or any combination thereof, etc. In some embodiments, the position/motion sensor 160 measures a displacement (e.g., angular displacement, linear displacement, or a combination thereof, etc.) of the monitoring device 152 over a period of time with reference to a three-dimensional coordinate system to determine an amount of activity performed by the user during a period of time. In some embodiments, a position sensor includes a biological sensor, which is further described below.

The vibrotactile module 164 provides sensory output to the user by vibrating portable device 152. Further, the communications module 166 is operable to establish wired or wireless connections with other electronic devices to exchange data (e.g., activity data, geo-location data, location data, a combination thereof, etc.). Examples of wireless communication devices include, but are not limited to, a Wi-Fi adapter, a Bluetooth device, an Ethernet adapter, and infrared adapter, an ultrasonic adapter, etc.

The touchscreen 206 may be any type of display with touch sensitive functions. In another embodiment, a display is included but the display does not have touch-sensing capabilities. The touchscreen may be able to detect a single touch, multiple simultaneous touches, gestures defined on the display, etc. The display driver 168 interfaces with the touchscreen 206 for performing input/output operations. In one embodiment, display driver 168 includes a buffer memory for storing the image displayed on touchscreen 206.

The buttons/user interface may include buttons, switches, cameras, USB ports, keyboards, or any other device that can provide input or output functions.

Device locator 172 provides capabilities for acquiring data related to the location (absolute or relative) of monitoring device 152. Examples device locators 172 include a GPS transceiver, a mobile transceiver, a dead-reckoning module, a camera, etc. As used herein, a device locator may be referred to as a device or circuit or logic that can generate geo-location data. The geo-location data provides the absolute coordinates for the location of the monitoring device 152. The coordinates may be used to place the monitoring device 152 on a map, in a room, in a building, etc. In some embodiments, a GPS device provides the geo-location data. In other embodiments, the geo-location data can be obtained or calculated from data acquired from other devices (e.g., cell towers, Wi-Fi device signals, other radio signals, etc.), which can provide data points usable to locate or triangulate a location.

External event analyzer 174 receives data regarding the environment of the user and determines external events that might affect the power consumption of the user. For example, the external event analyzer 174 may determine low light conditions in a room, and assume that there is a high probability that the user is sleeping. In addition, the external event analyzer 174 may also receive external data, such as GPS location from a smart phone, and determine that the user is on a vehicle and in motion.

In some embodiments, the processor 154 receives one or more geo-locations measured by the device locator 172 over a period of time and determines a location of the monitoring device 152 based on the geo-locations and/or based on one or more selections made by the user, or based on information available within a geo-location-location database of the network. For example, the processor 154 may compare the current location of the monitoring device against known locations in a location database, to identify presence in well-known points of interest to the user or to the community. In one embodiment, upon receiving the geo-locations from the device locator 172, the processor 154 determines the location based on the correspondence between the geo-locations and the location in the geo-location-location database.

The one or more environmental sensors 158 may sense and determine one or more environmental parameters (e.g., barometric pressure, weather condition, amount of light exposure, noise levels, radiation levels, magnetic field levels, or a combination thereof, etc.) of an environment in which the monitoring device is placed.

The watch 162 is operable to determine the amount of time elapsed between two or more events. In one embodiment, the events are associated with one or more positions sensed by the position sensor 160, associated with one or more environmental parameters determined by the environmental sensor 158, associated with one or more geo-locations determined by the device locator 172, and/or associated with one or more locations determined by the processor 154.

Power controller 178 manages and adjusts one or more power operational parameters defined for the monitoring device 152. In one embodiment, the power operational parameters include options for managing the touchscreen 206, such as by determining when to turn ON or OFF the touchscreen, scan rate, brightness, etc. In addition, the power controller 178 is operable to determine other power operational parameters, besides the parameters associated with the touchscreen, such as determining when to turn ON or OFF other modules (e.g., GPS, environmental sensors, etc.) or limiting the frequency of use for one or more of the modules within monitoring device 152.

Monitoring device 152 may have a variety of internal states and/or events which may dynamically change the characteristics of the touchscreen or of other modules. These states may include one or more of the following:

Battery level
Notifications/Prompting of user interaction
Alarm
Timer elapsed
Email received/sent
Instant Message received/sent
Text message received/sent
Calendar event
Physiological goal met (e.g. 10,000 steps reached in the day)
Non-physiological goal met (e.g. completed a to-do item)

Application notifications
Music player notifications (e.g. song ended/started, playlist ended/started)
User Interface
Layout of virtual buttons on the touchscreen
Expected user interaction based on what is displayed and/or the application in the foreground of the operating system.
   Expected user touch speed (e.g. fast for typing or playing a game, slow for reading an article)
   Expected user touch area
   Expected user touch trajectory (e.g. some games require long, straight swipes, while applications that take text input may require a touch to one specific area with little or no trajectory).
User interaction through non-touchscreen inputs
User pressing a button
User touching a capacitive touch sensor not integrated into the touchscreen
User activating a proximity sensor
Sensors which detect the user attempting to interact with the screen
   Force transducer under the screen
   Gyroscope, magnetometer, and/or accelerometer located near the screen
   Pressure transducer to measure change in pressure due to housing deflection when user presses on or near the screen
   Tap or initial touch detection using one or more or a combination of: accelerometers, piezoelectric sensors, motion sensors, pressure sensors, force sensors
User Characteristics
Gender
Age
Weight
Geographical location (e.g. urban area, rural area, country, city, town, exact address and or GPS coordinates)
   Current location
   Residence location
   Work location It is noted that these states may be communicated to the user through one or more methods including, but not limited to, displaying them visually, outputting an audio alert, and/or haptic feedback.

In some embodiments, data analysis of data produced by different modules may be performed in monitoring device 152, in other device in communication with monitoring device 152, or in combination of both devices. For example, the monitoring device may be generating a large amount of data related to the heart rate of the user. Before transmitting the data, the monitoring device 152 may process the large amount of data to synthesize information regarding the heart rate, and then the monitoring device 152 may send the data to a server that provides an interface to the user. For example, the monitoring device may provide summaries of the heart rate in periods of one minute, 30 seconds, five minutes, 50 minutes, or any other time period. By performing some calculations in the monitoring device 152, the processing time required to be performed on the server is decreased.

Some other data may be sent in its entirety to another device, such as steps the user is taken, or periodical updates on the location of the monitoring device 152. Other calculations may be performed in the server, such as analyzing data from different modules to determine stress levels, possible sickness by the user, etc.

It is noted that the embodiments illustrated in FIG. 10 are exemplary. Other embodiments may utilize different modules, additional modules, or a subset of modules. In addition, some of the functionality of two different modules might be combined in a single module, or the functionality of a single module might be spread over a plurality of components. The embodiments illustrated in FIG. 10 should therefore not be interpreted to be exclusive or limiting, but rather exemplary or illustrative.

Figure 11:
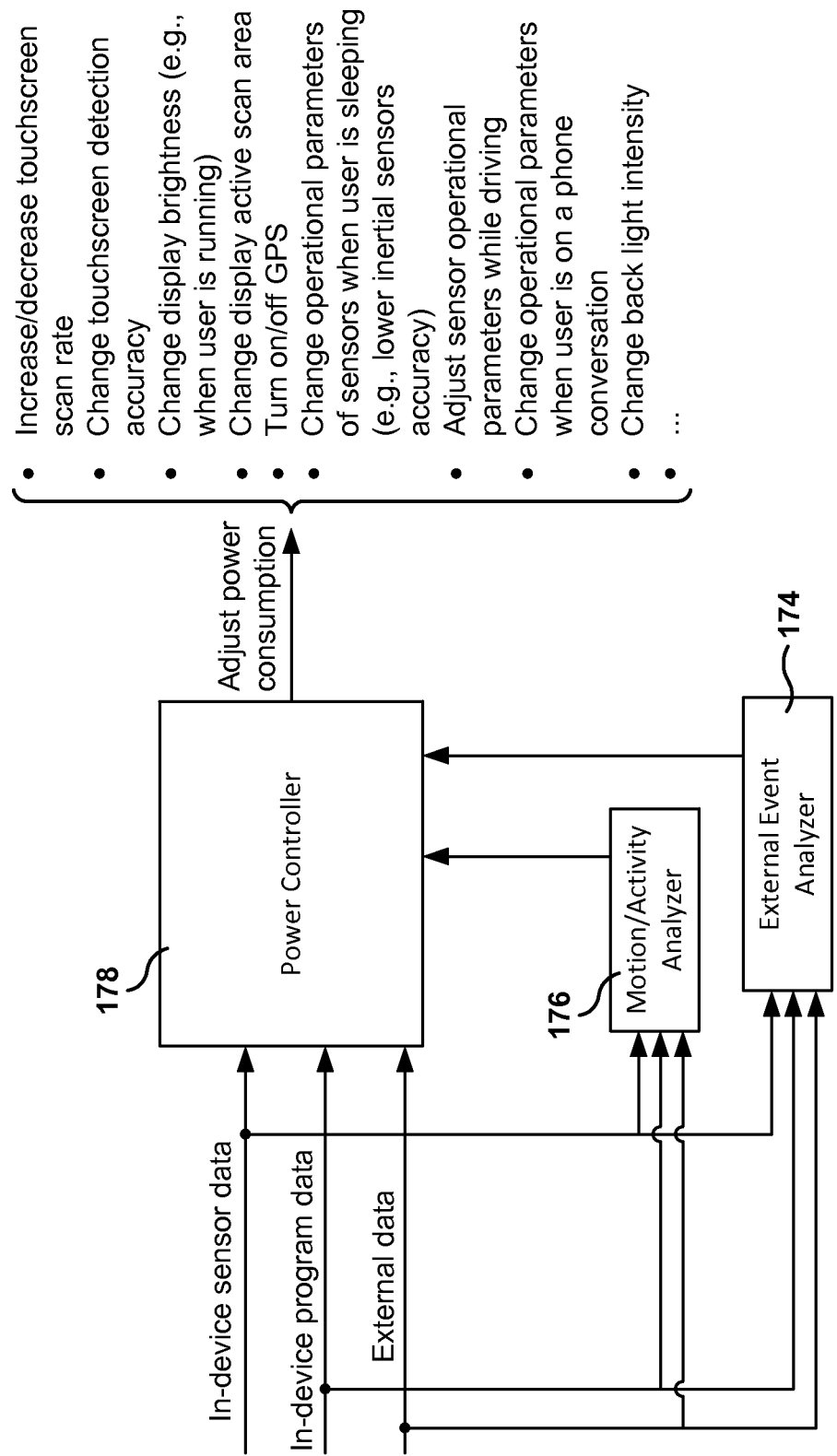
FIG. 11 illustrates a method for managing power consumption in a computing device, according to one embodiment.

FIG. 11 illustrates a method for managing power consumption in a computing device, according to one embodiment. Power controller 178 receives different types of data which may be generated by modules in the device, by programs in the device, or by external devices. In addition, the power controller 178 receives data from the motion/activity analyzer 176 and from external event analyzer 174. Power controller 178 analyzes all the data received to manage power consumption in the portable device.

As described above, the in-device sensor data may include step count, geographic location, accelerometer data etc. The in-device program data includes information created by programs running in the computer device, or in some other external device. For example, the program data may include a prediction of the trajectory of the gesture in the touchscreen, a state of the user (e.g., sleep or awake, etc.), or any other type of information that may assist the power controller 178 in managing power consumption in the electronic device.

The external data includes data received from other electronic devices, such as smart phones, heart monitors, GPS receivers, etc. For example, the external data may include the location of the user, a notification that the user has received a new email, the current heart rate of the user, a command entered in a smart phone for the monitoring device, etc.

The motion/activity analyzer 176 monitors the motion and/or the activity of the user. The motion/activity analyzer 176 may for example determine that the user has not moved for a long time, or that is late at night, and may determine that the user is sleeping. The findings from the motion/activity analyzer (e.g. motion and/or activity) are sent to power controller 178.

As discussed above, the external event analyzer 174 receives data regarding the environment of the user and determines external events that may affect the power consumption of the user. For example, the external event analyzer may determine that the user has just received an email or a text message. This information may be used to determine if an input is expected shortly from the user. The external data and or the events determined by the external event analyzer are transmitted to power controller 178.

Power controller 178 analyzes the data received from the different modules and determines actions to be performed to manage power consumption in the device. Depending on the situation, the power controller 178 may change the scan rate of the touchscreen, the resolution of the touchscreen, the brightness of the touchscreen, the amount of backlight, turn ON or OFF the GPS module, turn ON or OFF buttons on the display, etc.

In one embodiment, the actions to manage power by the power controller 178 may include one or more of the following actions described in Table 5 below.

TABLE 5

| Action to manage power |
| --- |
| Increase or decrease the touchscreen scan rate |
| Change touchscreen detection accuracy. |
| Change display brightness (e.g., when user is running). |
| Change display active scan area (e.g., see FIG. 3). |
| Turn on or off GPS. |

TABLE 5-continued

Action to manage power

Change the operational parameters of sensors when the user is sleeping (e.g., lower inertial sensors accuracy).
Adjust sensor operational parameters while user is driving or in a moving vehicle.
Change operational parameters when the user is on a phone conversation.
Change back light intensity, etc.

It is noted that the embodiments illustrated in FIG. 11 are exemplary. Other embodiments may utilize different inputs or outputs, different modules, or perform different power management operations. The embodiments illustrated in FIG. 11 should therefore not be interpreted to be exclusive or limiting, but rather exemplary or illustrative.

Figure 12:
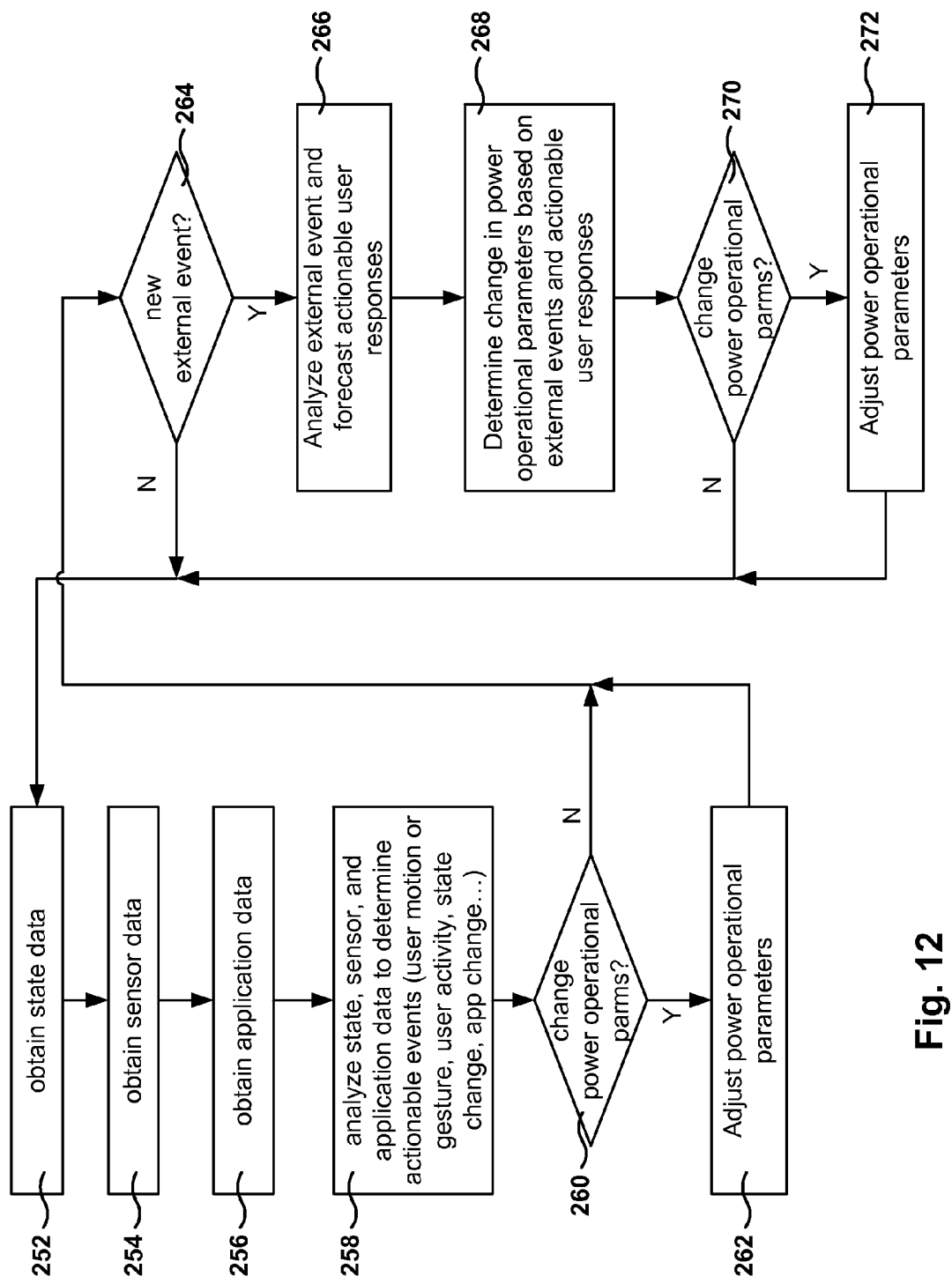
FIG. 12 is a flowchart describing a method for power management, according to one embodiment.

FIG. 12 is a flowchart describing a method for power management, according to one embodiment. While the various operations in this flowchart are presented and described sequentially, one of ordinary skill will appreciate that some or all of the operations may be executed in a different order, be combined or omitted, or be executed in parallel.

In operation 252, the power controller module obtains data related to the state of the portable device. The data regarding state may include a plurality of different possible states, as described above, such as user is sleeping, user is running, user has received a new email, user arrives home, user arrives at work, etc.

From operation 252, the method flows to operation 254 where the data from the different sensors in the portable device is obtained. The data may include the number of steps taken by the user in a period of time, the environmental temperature, whether the portable device is in motion or has been stationary for a period of time, etc. In one embodiment, the sensor data may be used to change the state data obtained in operation 252.

From operation 254, the method flows to operation 256 where data from applications, executed in the portable device or in an external portable device, is obtained. The data from applications refers to events identified by the applications. For example, the application data may include events such as the user has received an email, the user has received a text message, the user has received a phone call, the user is moving at 60 miles an hour, an alarm set by the user has occurred or is about to occur in a short period of time, etc.

From operation 256, the method flows to operation 258 where state, sensor, and application data are analyzed to determine actionable events to manage power consumption by the portable device. For example, the analysis may determine that the user is in motion, that the user has performed a touch gesture, a user activity (e.g., running, climbing stairs), that the user has changed state (e.g., the user has awoken), that an application change may require a power adjustment (e.g., the user has received a text message and is about to check the display, a vibrating alarm has indicated to the user that an external event has occurred and the user may soon respond to the external event, etc.), etc.

From operation 258, the method flows to operation 260 to check if a change is needed in the power operational parameters of the portable device based on the analysis of operation 258. If a change in the power operational parameter is required, the method flows to operation 262, and if a change is not required the method flows to operation 264.

In operation 262, the power operational parameters of the portable device are adjusted based on the analysis performed in operation 258. The power operational parameters that can be changed may include a scan rate of the touchscreen, display ON or OFF, display brightness, turning sensors on or off, etc.

From operation 262, the method flows to operation 264, where a check is made to determine if a new external event has been received. If a new external event has been received the method flows to operation 2662 to analyze the new external event, and if a new external event has not been received the method flows back to operation 252.

In operation 266, the method analyzes the external event and performs a forecast of actionable user responses to the external event. In one embodiment, the analysis in operation 266 also takes into account the data obtained in operations 252, 254, and 256.

From operation 266, the method flows to operation 268 to determine if any power operational parameters needs to be changed, based on the external events received or in actionable user responses.

From operation 268, the method flows to operation 270 where a check is made to determine if the power operational parameters need to change. If the power operational parameters have to be changed, the method flows to operation 272, and if the power operational parameters do not have to change the method flows back to operation 252.

In operation 272, the power operational parameters are adjusted based on the determination made in operation 268, and afterwards the method flows back to operation 252.

Figure 13:
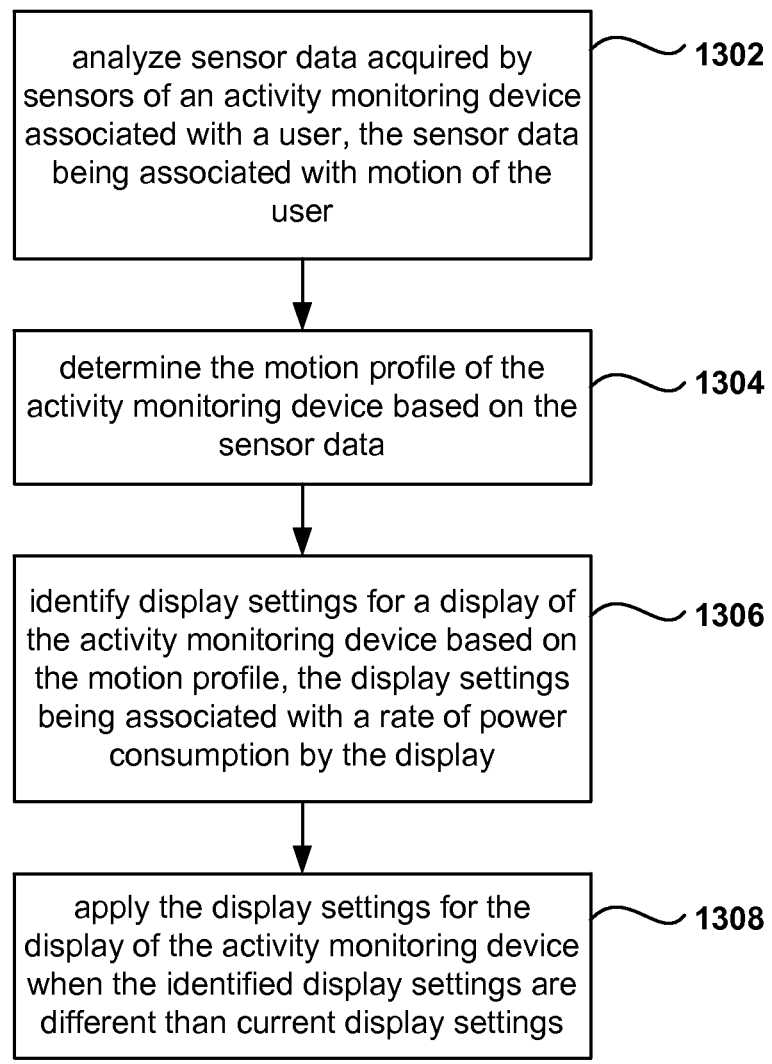
FIG. 13 is a flowchart of a method for managing power consumption in an activity monitoring device, according to one embodiment.

FIG. 13 is a flowchart of a method for managing power consumption in a portable device, according to one embodiment. While the various operations in this flowchart are presented and described sequentially, one of ordinary skill will appreciate that some or all of the operations may be executed in a different order, be combined or omitted, or be executed in parallel.

In operation 1302, sensor data is analyzed. The sensor data is acquired by sensors of an activity monitoring device associated with a user, and the sensor data is associated with motion of the user.

From operation 1302, the method flows to operation 1304 where a motion profile of the activity monitoring device is determined based on the sensor data. From operation 1304, the method flows to operation 1306 to identify the display settings for a display of the activity monitoring device based on the motion profile. The display settings are associated with a rate of power consumption by the display.

From operation 1306, the method flows to operation 1308 to apply the display settings for the display of the activity monitoring device when the identified display settings are different than current display settings.

In one embodiment, the operations of method of FIG. 13 are executed by a processor.

Figure 14:
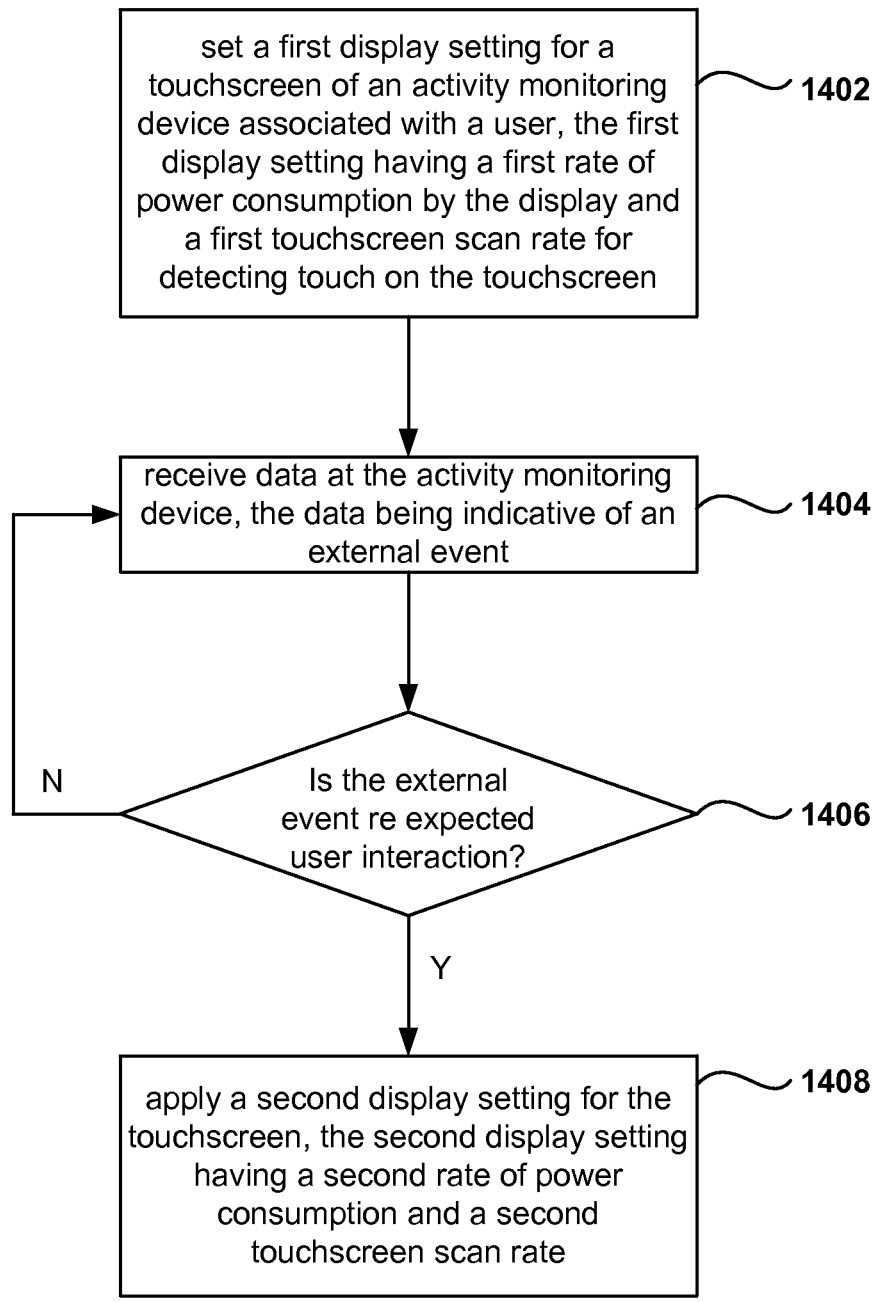
FIG. 14 is a flowchart of a method for adjusting display behavior based on an expectation of user interaction, according to one embodiment.

FIG. 14 is a flowchart of a method for adjusting display behavior based on an expectation of user interaction, according to one embodiment. While the various operations in this flowchart are presented and described sequentially, one of ordinary skill will appreciate that some or all of the operations may be executed in a different order, be combined or omitted, or be executed in parallel.

In operation 1402, the method sets a first display setting for a touchscreen of an activity monitoring device associated with a user. The first display setting has a first rate of power consumption by the display and a first touchscreen scan rate for detecting touch on the touchscreen.

Operation 1402, the method flows to operation 1404 where data is received at the activity monitoring device, where the data is indicative of an external event. From operation 1404, the method flows to operation 1406 where a check is made to determine if the external event is associated with a predefined expected user interaction with the touchscreen.

If user interaction is expected, the method flows to operation 1408, and if user interaction is not expected the method flows back to operation 1404. In operation 1408, the method applies a second display setting for the touchscreen based on the predefined expected user interaction. The second display setting has a second rate of power consumption and a second touchscreen scan rate.

Figure 15:
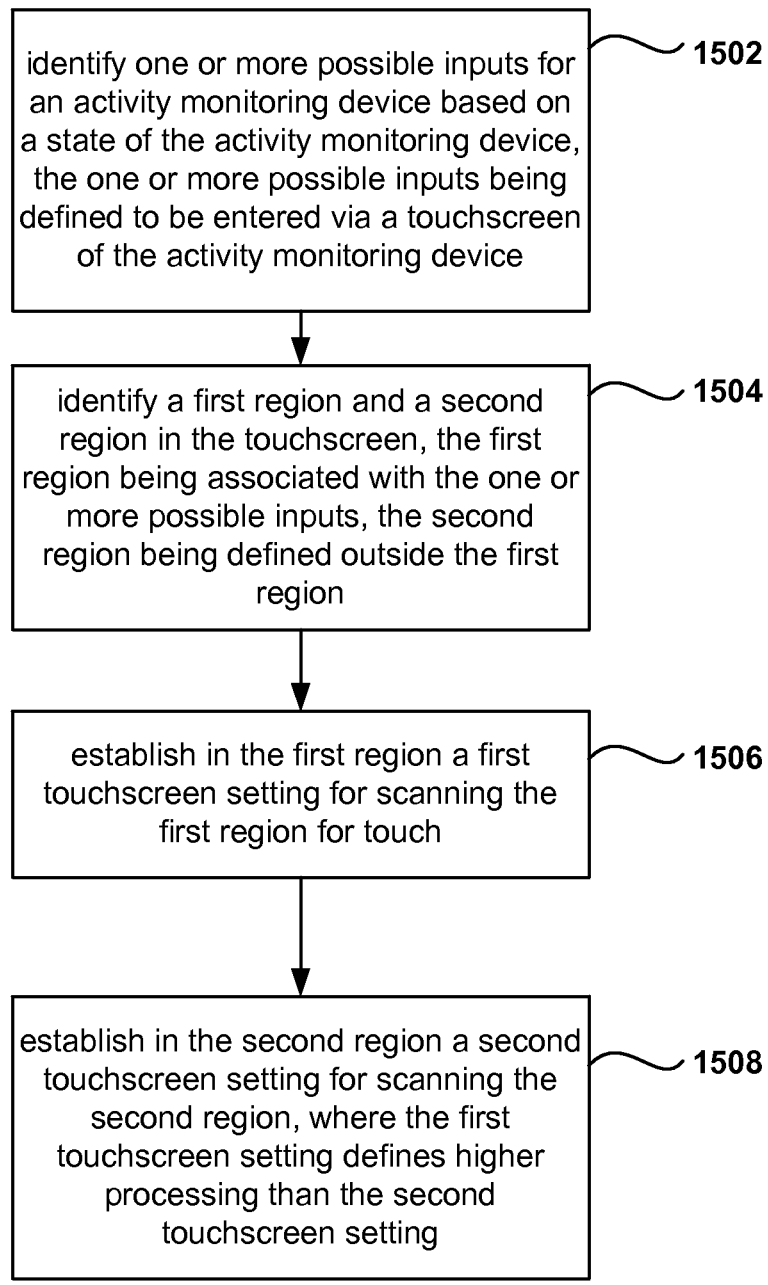
FIG. 15 is a flowchart of a method for setting different areas on the display with different scan rates based on the Graphical User Interface (GUI), according to one embodiment.

FIG. 15 is a flowchart of a method for setting different areas on the display with different scan rates based on the Graphical User Interface (GUI), according to one embodiment. While the various operations in this flowchart are presented and described sequentially, one of ordinary skill will appreciate that some or all of the operations may be executed in a different order, be combined or omitted, or be executed in parallel.

In operation 1502, the method identifies one or more possible inputs for an activity monitoring device based on a state of the activity monitoring device. The one or more possible inputs are defined to be entered via a touchscreen of the activity monitoring device.

From operation 1502, the method flows to operation 1504 where a first region and a second region are identified in the touchscreen, where the first region is associated with the one or more possible inputs, and the second region is defined outside the first region.

Further, from operation 1504, the method flows to operation 1506 to establish in the first region a first touchscreen setting for scanning the first region for touch. From operation 1506, the method flows to operation 1508 to establish in the second region a second touchscreen setting for scanning the second region, where the first touchscreen setting defines higher processing than the second touchscreen setting.

Figure 16:
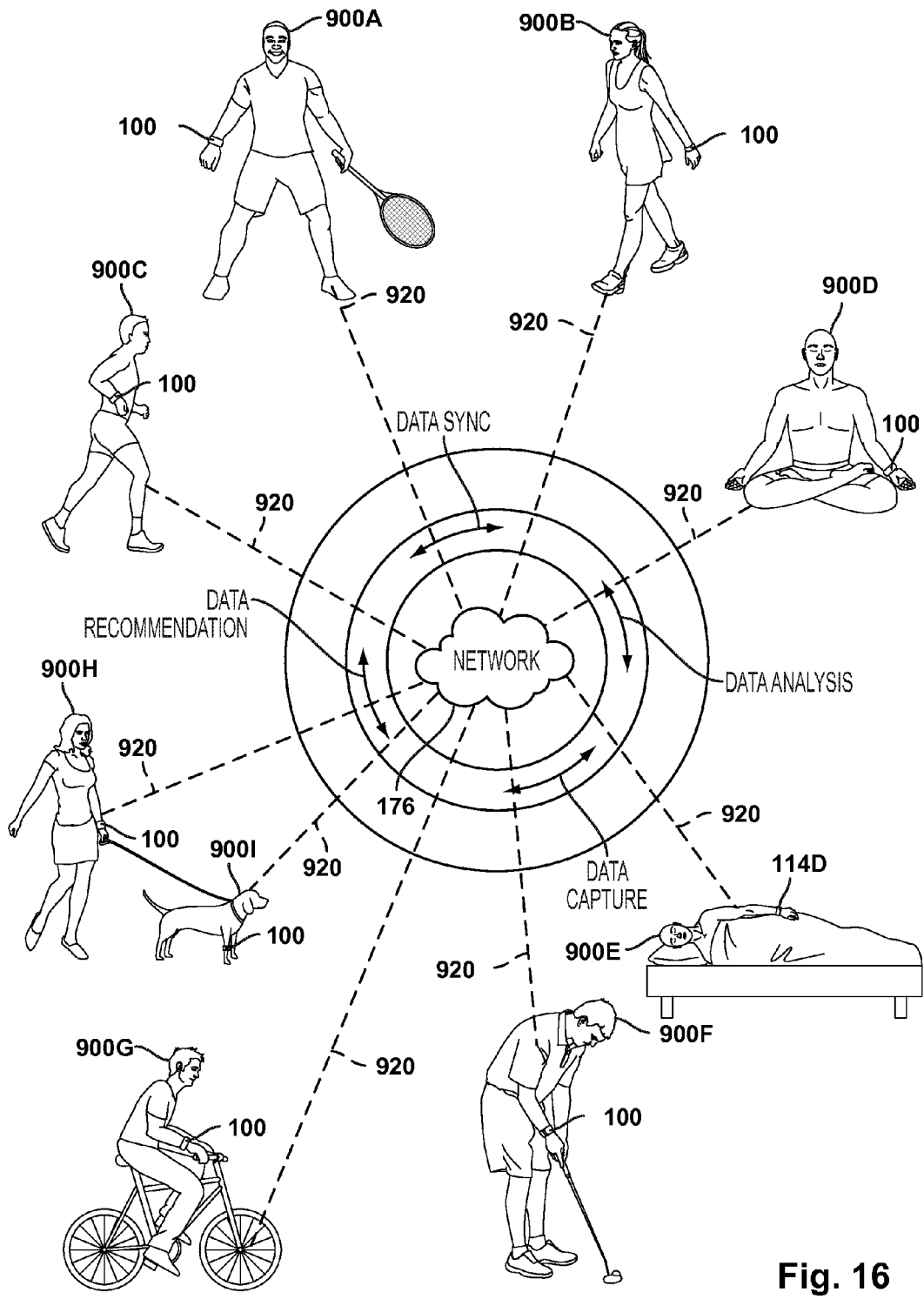
FIG. 16 illustrates an example where various types of activities of users can be captured or collected by activity tracking devices, in accordance with various embodiments of the present invention.

FIG. 16 illustrates an example where various types of activities of users 900A-900I can be captured or collected by activity tracking devices, in accordance with various embodiments of the present invention. As shown, the various types of activities can generate different types of data that can be captured by the activity tracking device 100. The data, which can be represented as motion data (or processed motion data) can be transferred 920 to a network 176 for processing and saving by a server, as described above. In one embodiment, the activity tracking device 100 can communicate to a device using a wireless connection, and the device is capable of communicating and synchronizing the captured data with an application running on the server. In one embodiment, an application running on a local device, such as a smart phone or tablet or smart watch can capture or receive data from the activity tracking device 100 and represent the tract motion data in a number of metrics.

In one embodiment, the device collects one or more types of physiological and/or environmental data from embedded sensors and/or external devices and communicates or relays such metric information to other devices, including devices capable of serving as Internet-accessible data sources, thus permitting the collected data to be viewed, for example, using a web browser or network-based application. For example, while the user is wearing an activity tracking device, the device may calculate and store the user's step count using one or more sensors. The device then transmits data representative of the user's step count to an account on a web service, computer, mobile phone, or health station where the data may be stored, processed, and visualized by the user. Indeed, the device may measure or calculate a plurality of other physiological metrics in addition to, or in place of, the user's step count.

Some physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Still further, other metrics can include, without limitation, calories burned by a user, weight gained by a user, weight lost by a user, stairs ascended, e.g., climbed, etc., by a user, stairs descended by a user, steps taken by a user during walking or running, a number of rotations of a bicycle pedal rotated by a user, sedentary activity data, driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active. In some embodiments, a user may stand on a monitoring device that determines a physiological parameter of the user. For example, a user stands on a scale that measures a weight, a body fat percentage, a biomass index, or a combination thereof, of the user.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive.

This information can be associated to the users account, which can be managed by an activity management application on the server. The activity management application can provide access to the users account and data saved thereon. The activity manager application running on the server can be in the form of a web application. The web application can provide access to a number of websites screens and pages that illustrate information regarding the metrics in various formats. This information can be viewed by the user, and synchronized with a computing device of the user, such as a smart phone.

In one embodiment, the data captured by the activity tracking device 100 is received by the computing device, and the data is synchronized with the activity measured application on the server. In this example, data viewable on the computing device (e.g. smart phone) using an activity tracking application (app) can be synchronized with the data present on the server, and associated with the user's account. In this way, information entered into the activity tracking application on the computing device can be synchronized with application illustrated in the various screens of the activity management application provided by the server on the website.

The user can therefore access the data associated with the user account using any device having access to the Internet. Data received by the network 176 can then be synchronized with the user's various devices, and analytics on the server can provide data analysis to provide recommendations for additional activity, and or improvements in physical health. The process therefore continues where data is captured, analyzed, synchronized, and recommendations are produced. In some embodiments, the captured data can be itemized and partitioned based on the type of activity being performed, and such information can be provided to the user on the website via graphical user interfaces, or by way of the application executed on the users smart phone (by way of graphical user interfaces).

In an embodiment, the sensor or sensors of a device 100 can determine or capture data to determine an amount of movement of the monitoring device over a period of time. The sensors can include, for example, an accelerometer, a magnetometer, a gyroscope, or combinations thereof. Broadly speaking, these sensors are inertial sensors, which capture some movement data, in response to the device 100 being moved. The amount of movement (e.g., motion sensed) may occur when the user is performing an activity of climbing stairs over the time period, walking, running, etc. The monitoring device may be worn on a wrist, carried by a user, worn on clothing (using a clip, or placed in a pocket), attached to a leg or foot, attached to the user's chest, waist, or integrated in an article of clothing such as a shirt, hat, pants, blouse, glasses, and the like. These examples are not limiting to all the possible ways the sensors of the device can be associated with a user or thing being monitored.

In other embodiments, a biological sensor can determine any number of physiological characteristics of a user. As another example, the biological sensor may determine heart rate, a hydration level, body fat, bone density, fingerprint data, sweat rate, and/or a bioimpedance of the user. Examples of the biological sensors include, without limitation, a biometric sensor, a physiological parameter sensor, a pedometer, or a combination thereof.

In some embodiments, data associated with the user's activity can be monitored by the applications on the server and the users device, and activity associated with the user's friends, acquaintances, or social network peers can also be shared, based on the user's authorization. This provides for the ability for friends to compete regarding their fitness, achieve goals, receive badges for achieving goals, get reminders for achieving such goals, rewards or discounts for achieving certain goals, etc.

As noted, an activity tracking device 100 can communicate with a computing device (e.g., a smartphone, a tablet computer, a desktop computer, or computer device having wireless communication access and/or access to the Internet). The computing device, in turn, can communicate over a network, such as the Internet or an Intranet to provide data synchronization. The network may be a wide area network, a local area network, or a combination thereof. The network may be coupled to one or more servers, one or more virtual machines, or a combination thereof. A server, a virtual machine, a controller of a monitoring device, or a controller of a computing device is sometimes referred to herein as a computing resource. Examples of a controller include a processor and a memory device.

In one embodiment, the processor may be a general purpose processor. In another embodiment, the processor can be a customized processor configured to run specific algorithms or operations. Such processors can include digital signal processors (DSPs), which are designed to execute or interact with specific chips, signals, wires, and perform certain algorithms, processes, state diagrams, feedback, detection, execution, or the like. In some embodiments, a processor can include or be interfaced with an application specific integrated circuit (ASIC), a programmable logic device (PLD), a central processing unit (CPU), or a combination thereof, etc.

In some embodiments, one or more chips, modules, devices, or logic can be defined to execute instructions or logic, which collectively can be viewed or characterized to be a processor. Therefore, it should be understood that a processor does not necessarily have to be one single chip or module, but can be defined from a collection of electronic or connecting components, logic, firmware, code, and combinations thereof.

Examples of a memory device include a random access memory (RAM) and a read-only memory (ROM). A memory device may be a Flash memory, a redundant array of disks (RAID), a hard disk, or a combination thereof.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relate to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure are not to be limited to the details given herein, but may be modified within the scope and equivalents of the appended claims.

What is claimed is:

1. A method comprising:
setting a first display setting for a touchscreen of an activity monitoring device associated with a user, the first display setting having a first rate of power consumption by the display and a first touchscreen scan rate for detecting touch on the touchscreen;
receiving data at the activity monitoring device, the data being indicative of an external event; and
applying a second display setting for the touchscreen based on a predefined expected user interaction, the second display setting having a second rate of power consumption and a second touchscreen scan rate, wherein operations of the method are executed by a processor.

2. The method as recited in claim 1, further including:
determining if the external event is associated with a predefined expected user interaction with the touchscreen.

3. The method as recited in claim 2, wherein the external event is defined by one or more of a notification, a message, an alert, an email, an alarm, a text message, a time, an incoming phone call, an incoming video call, a post on a social network, a location, an instruction for navigation, or a combination thereof, and thus is associated with information for presentation on the touchscreen.

4. The method as recited in claim 1, wherein the external event is originated, detected or obtained by a mobile phone, wherein the mobile phone transmits the data associated with the external event to the activity monitoring device.

5. The method as recited in claim 1, wherein the second display setting further includes parameters for one or more of a touchscreen detection accuracy, or a display brightness, or a display active scan area, or a back light intensity.

6. The method as recited in claim 1, wherein determining if the external event is associated with a predefined expected user interaction:
determining a state of the user, the state of the user being selected from a group consisting of running, or being stationary, or driving, or climbing steps, or walking, or sleeping.

7. The method as recited in claim 1, wherein the first display setting is set when immediate interaction with the user is not expected.

8. The method as recited in claim 1, wherein the data is received from one of a tablet, a personal computer, or a laptop.

9. The method as recited in claim 1, wherein the data is received from a server on a network.

10. The method as recited in claim 1, wherein the second touchscreen scan rate is greater than the first touchscreen scan rate.

11. The method as recited in claim 1, wherein the second rate of power consumption is greater than the first rate of power consumption.

12. The method as recited in claim 1, wherein the external event indicates an elevated heart rate of the user.

13. The method as recited in claim 1, wherein operations of the method are performed by a computer program when executed by one or more processors, the computer program being embedded in a non-transitory computer-readable storage medium.

14. A method comprising:
setting a first display setting for a touchscreen of an activity monitoring device associated with a user;
receiving data at the activity monitoring device, the data being indicative of an external event;
presenting a notification message on the touchscreen regarding the external event;
determining if the external event is associated with a predefined expected user interaction with the touchscreen; and
applying a second display setting for the touchscreen based on the predefined expected user interaction, wherein applying the second display setting further includes,
setting, in a first area of the touchscreen where touch is expected, a first touchscreen scan rate for detecting touch on the touchscreen; and
setting, in a second area of the touchscreen where touch is not expected, a second touchscreen scan rate, wherein operations of the method are executed by a processor.

15. The method as recited in claim 14 further including:
entering a vibration mode for the activity monitoring device after presenting the notification message.

16. The method as recited in claim 14, wherein the notification message is one or more of an alarm, or a timer elapsed, or an email received, or an instant message received, or a text message received, or a calendar event, or a physiological goal met, or a non-physiological goal met, or an application notification, or a music player notification.

17. The method as recited in claim 14, wherein the first touchscreen scan rate is greater than zero, wherein the second touchscreen scan rate is equal to zero.

18. The method as recited in claim 14, wherein applying the second display setting further includes:
identifying one or more of an expected user touch speed or an expected touch trajectory.

19. The method as recited in claim 14 further including:
resetting the first display setting after a predetermined timeout period without user interaction.

20. A method comprising:
setting a first display setting for a touchscreen of an activity monitoring device when the activity monitoring device is not interacting with a user;
receiving, at the activity monitoring device, data indicating that the user has received a communication from another user; and
setting a second display setting for the touchscreen, the second display setting including an interface in the touchscreen that enables selection of an option for viewing details of the communication, the interface including a subregion of the touchscreen for selecting the option for viewing details, wherein setting the second display setting further includes,
setting in the subregion a first touchscreen scan rate for detecting touch on the touchscreen; and
setting a second touchscreen scan rate in areas of the touchscreen outside the subregion, wherein operations of the method are executed by a processor.

21. The method as recited in claim 20, wherein the subregion is defined by a button on the display.

22. The method as recited in claim 20, wherein the subregion is defined by a text message on the display.

23. The method as recited in claim 20, wherein the second touchscreen scan rate is zero.

24. The method as recited in claim 20, further including:
defining a plurality of areas on the touchscreen, wherein each area is associated with a touch input area on the touchscreen.

25. The method as recited in claim 20, wherein operations of the method are performed by a computer program when executed by one or more processors, the computer program being embedded in a non-transitory computer-readable storage medium.

26. An activity monitoring device comprising:
one or more biometric sensors for capturing biometric data of a user wearing the activity monitoring device;
a network communications module for sending and receiving data;
a memory for storing a computer program, biometric data, and communications data;
a display with a touchscreen; and
a processor for setting a first display setting for the touchscreen, the first display setting having a first rate of power consumption by the display and a first touchscreen scan rate for detecting touch on the touchscreen, the processor applying a second display setting for the touchscreen based on a predefined expected user interaction, wherein the second display setting has a second rate of power consumption and a second touchscreen scan rate.

27. The activity monitoring device as recited in claim 26, wherein the activity monitoring device is a smart watch.

28. The activity monitoring device as recited in claim 26, further including:
one or more motion sensors; and
one or more environmental sensors.

29. The activity monitoring device as recited in claim 26, wherein the processor determines if data received at the activity monitoring device is indicative of an external event associated with a predefined expected user interaction with the touchscreen.

30. The activity monitoring device as recited in claim 26, wherein the network communications module is one or more of a mobile telephony communications module, or a WiFi module, or a Bluetooth module, or a Bluetooth low energy module.

* * * * *